(12) United States Patent
Debnath et al.

(10) Patent No.: US 10,137,107 B2
(45) Date of Patent: Nov. 27, 2018

(54) SUBSTITUTED PHENYLPYRROLECARBOXAMIDES WITH THERAPEUTIC ACTIVITY IN HIV

(71) Applicants: New York Blood Center, Inc., New York, NY (US); The United States of America, as Represented by the Secretary, Department of Health and Human Services, Washington, DC (US)

(72) Inventors: Asim Kumar Debnath, Fort Lee, NJ (US); Francesca Curreli, Bronx, NY (US); Peter D. Kwong, Bethesda, MD (US); Young Do Kwon, Bethesda, MD (US)

(73) Assignees: New York Blood Center, Inc., New York, NY (US); National Institutes of Health, Bethesda, MD (US)

( * ) Notice: Subject to any disclaimer, the term of this patent is extended or adjusted under 35 U.S.C. 154(b) by 0 days.

(21) Appl. No.: 15/512,493

(22) PCT Filed: Sep. 18, 2015

(86) PCT No.: PCT/US2015/051086
§ 371 (c)(1),
(2) Date: Mar. 17, 2017

(87) PCT Pub. No.: WO2016/044808
PCT Pub. Date: Mar. 24, 2016

(65) Prior Publication Data
US 2017/0273943 A1    Sep. 28, 2017

Related U.S. Application Data

(60) Provisional application No. 62/209,619, filed on Aug. 25, 2015, provisional application No. 62/209,268, filed on Aug. 24, 2015, provisional application No. 62/052,974, filed on Sep. 19, 2014.

(51) Int. Cl.
| | | |
|---|---|---|
| *C07D 403/12* | (2006.01) |
| *A61K 31/40* | (2006.01) |
| *C07D 405/14* | (2006.01) |
| *C07D 417/12* | (2006.01) |
| *C07D 417/14* | (2006.01) |
| *C07D 207/34* | (2006.01) |
| *C07C 25/00* | (2006.01) |
| *C07C 233/01* | (2006.01) |
| *C07D 207/30* | (2006.01) |
| *C07D 277/20* | (2006.01) |
| *A61P 31/18* | (2006.01) |

(52) U.S. Cl.
CPC .............. *A61K 31/40* (2013.01); *A61P 31/18* (2018.01); *C07C 25/00* (2013.01); *C07C 233/01* (2013.01); *C07D 207/30* (2013.01); *C07D 207/34* (2013.01); *C07D 277/20* (2013.01); *C07D 403/12* (2013.01); *C07D 405/14* (2013.01); *C07D 417/12* (2013.01); *C07D 417/14* (2013.01)

(58) Field of Classification Search
CPC ..... C07D 207/30; C07D 277/20; A61K 31/40
USPC ......................................... 514/91
See application file for complete search history.

(56) References Cited

U.S. PATENT DOCUMENTS

| 5,262,567 A | 11/1993 | Callens |
| 9,309,237 B2 | 4/2016 | Debnath |
| 2003/0207913 A1 | 10/2003 | Piotrowski |
| 2011/0144103 A1 | 6/2011 | Chimmanamada |

FOREIGN PATENT DOCUMENTS

WO     2013/036676 A1    3/2013

OTHER PUBLICATIONS

Scalzo et al. European Journal of Medicinal Chemistry (1988), 23(6), 587-91.*
PUBCHEM-CID-60964721 Create Date: Oct. 19, 2012 (Oct. 19, 2012) p. 3, Fig.
PubChem CID: 71510812 Create Date: Jun. 10, 2013 (Jun. 10, 2013) p. 3, Fig.
Cara et al. Phenylpyrrole derivatives as neural and inducible nitric oxide synthase (nNOS and iNOS) inhibitors, European Journal of Medicinal Chemistry, 2009, vol. 44, Issue 6, pp. 2655-2666.
Curreli et al., J. Med. Chem. 58(17):6909-6927, 2015.

* cited by examiner

*Primary Examiner* — Kahsay Habte
(74) *Attorney, Agent, or Firm* — K&L Gates LLP; Louis C. Cullman; David Diamond

(57) ABSTRACT

Substituted phenylpyrrolecarboxamide compounds such as those represented by Formula A can be used in the treatment of HIV infection and related conditions.

18 Claims, No Drawings

SUBSTITUTED PHENYLPYRROLECARBOXAMIDES WITH THERAPEUTIC ACTIVITY IN HIV

STATEMENT REGARDING FEDERALLY SPONSORED RESEARCH OR DEVELOPMENT

This invention was made with government support under Grant/Contract Number 1R01AI104416-01A1 awarded by the National Institutes of Health. The government has certain rights in the invention

BACKGROUND

Human immunodeficiency virus (HIV) is known to cause AIDS. Human immunodeficiency virus type 1 (HIV-1) cell entry process is thought to start when its surface envelope glycoproteins gp120 bind to the host cell primary receptor CD4. The binding triggers conformational changes in gp120 that facilitate its binding to the host cell coreceptor (secondary) CCR5 or CXCR4. There is no drug available yet that targets HIV-1 gp120.

Phe43 cavity of HIV-1 gp120 may be a target for developing entry inhibitors for AIDS therapy and prophylaxis.

SUMMARY

Disclosed herein are anti-HIV compounds.

Some embodiments include a pharmaceutical composition, such as an antiviral composition, comprising a compound represented by the following formula:

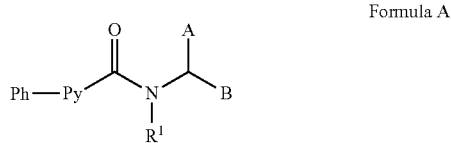

Formula A wherein Ph is optionally substituted phenyl; Py is optionally substituted pyrrolyl; or Ph-Py is optionally substituted indolyl; $R^1$ is H or $C_{1-6}$ hydrocarbyl; A is H, optionally substituted imidazolyl, optionally substituted thiazolyl, optionally substituted pyrrolyl, morpholine-4-carbonyl, ((2-(methylsulfonamido)ethyl)carbamoyl), optionally substituted piperazin-1-ylcarbamoyl, or optionally substituted morpholinocarbamoyl, or (2-hydroxyethyl)carbamoyl); and B is optionally substituted aminomethyl, optionally substituted amino($C_{1-3}$ alkyl) (such as optionally substituted aminomethyl, aminoethyl, aminopropyl, etc.), optionally substituted alkylamino($C_{1-3}$)alkyl (such as —$CH_2NHCH_3$, —$CH_2N(CH_3)_2$, —$CH_2CH_2NHCH_3$, —$CH_2CH_2N(CH_3)_2$, acetaminomethyl, piperidinyl, optionally substituted guanidino, optionally substituted guanidino($C_{1-3}$ alkyl) (such as optionally substituted guanidinomethyl, optionally substituted guanidinoethyl, or optionally substituted guanidinopropyl), optionally substituted phenyl, optionally substituted furanyl, optionally substituted triazolyl, optionally substituted pyrazolyl, or optionally substituted phenylmethyl; or

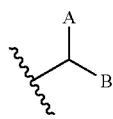

is optionally substituted pyrimidinyl.

Some embodiments include a method of inhibiting HIV comprising administering a compound described herein to a human being infected with HIV virus.

Some embodiments include a method of treating HIV infection comprising administering a compound described herein to a human being infected with HIV virus.

DETAILED DESCRIPTION

Disclosed herein are compounds useful for treating and preventing HIV infection, and methods of using of those compounds. Some of the compounds described herein may target and inhibit gp120 from binding to the host cell receptor, CD4.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms in a parent compound or structural feature. The term "replaces" is merely used herein for convenience, and does not require that the compound be formed by replacing one atom with another. In some embodiments, a substituent may be any ordinary organic moiety known in the art, which may have a molecular weight (e.g. the sum of the atomic masses of the atoms of the substituent) of 15 Da to 50 Da, 15 Da to 100 Da, 15 Da to 150 Da, 15 Da to 200 Da, 15 Da to 300 Da, or 15 Da to 500 Da. In some embodiments, a substituent comprises, or consists of: 0-30, 0-20, 0-10, or 0-5 carbon atoms; 0-62, 0-41, 0-21, or 0-11 hydrogen atoms; and 0-30, 0-20, 0-10, or 0-5 heteroatoms, wherein each heteroatom may independently be: N, O, P, S, Si, F, Cl, Br, or I; provided that the substituent includes one C, N, O, P, S, Si, F, Cl, Br, or I atom.

Examples of substituents include, but are not limited to, hydrocarbyl, such as alkyl, alkenyl, alkynyl; heteroalkyl, including any moiety wherein one or more heteroatoms replaces one or more carbon atoms of an alkyl moiety, and some accompanying hydrogen atoms (e.g. N replaces CH, O replaces $CH_2$, Cl replaces $CH_3$, etc.), such as alkoxy, alkylthio, haloalkyl, haloalkoxy, amino, etc.; heteroalkenyl, including any moiety wherein one or more heteroatoms replaces one or more carbon atoms of an alkenyl moiety, and some accompanying hydrogen atoms, such as acyl, acyloxy, thiocarbonyl, alkylcarboxylate, O-carbamyl, N-carbamyl, O-thiocarbamyl, N-thiocarbamyl, C-amido, N-amido, sulfinyl, isocyanato, isothiocyanato, etc; heteroalkynyl, including any moiety wherein one or more heteroatoms replaces one or more carbon atoms of an alkynyl moiety, and some accompanying hydrogen atoms, such as cyano, thiocyanato, cyanato, etc.; aryl; heteroaryl; hydroxy; aryloxy; thiol; halo; S-sulfonamido; N-sulfonamido; nitro; silyl; sulfonyl; trihalomethanesulfonyl; trihalomethanesulfonamido; etc.

For convenience, the term "molecular weight" is used with respect to a moiety or part of a molecule to indicate the sum of the atomic masses of the atoms in the moiety or part of a molecule, even though it may not be a complete molecule. If a substituent is anionic or cationic, only the covalently bonded atoms are counted in the molecular weight. Although counter-ions can be present, they are not included in the determination of molecular weight. Thus, —$CO_2^-Na^+$ would be considered have a molecular weight of about 44 Da and not about 67 Da.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by

attachment may occur at any position normally occupied by a hydrogen atom.

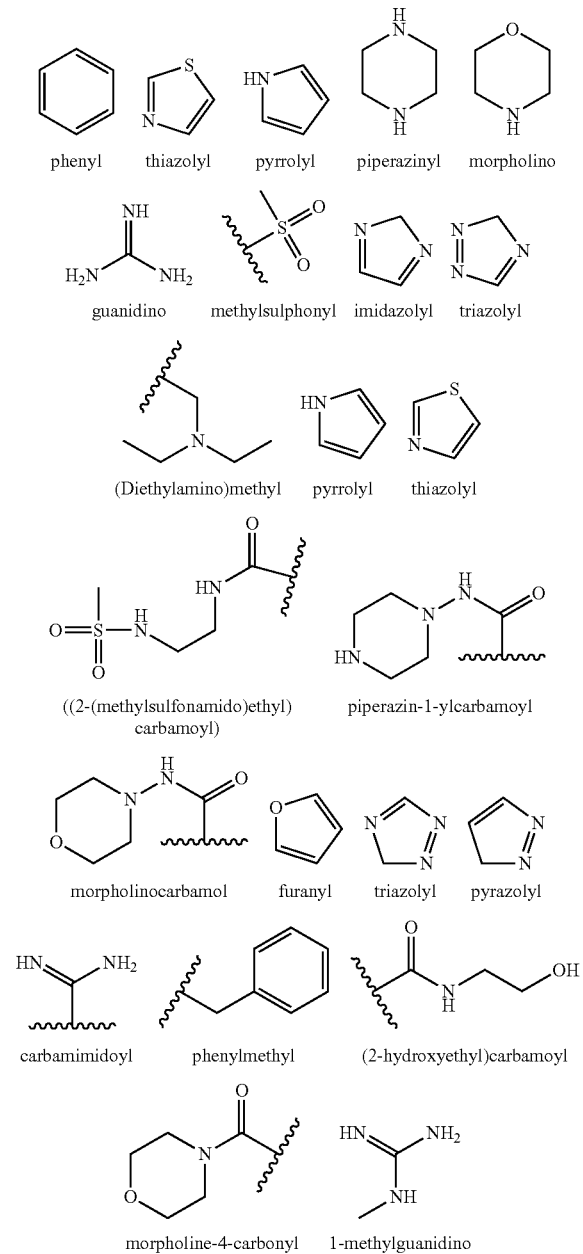

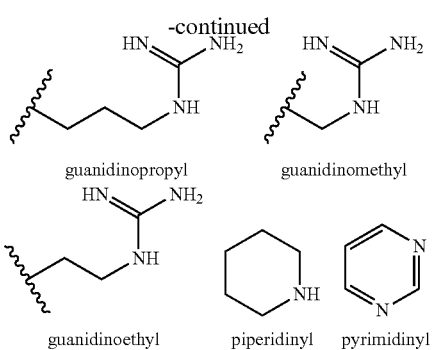

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. branched heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), and the like.

As used herein the term "aryl" has the broadest meaning generally understood in the art, and includes a ring or a ring system having at least one aromatic ring, such as phenyl, naphthyl, etc.

The term "heteroaryl" also has the meaning understood by a person of ordinary skill in the art, and in some embodiments, may refer to an "aryl" that has one or more heteroatoms in the ring or ring system. Examples of "heteroaryl" may include, but are not limited to, pyridinyl, furyl, thienyl, oxazolyl, thiazolyl, imidazolyl, indolyl, quinolinyl, benzofuranyl, benzothienyl, benzooxazolyl, benzothiazolyl, benzoimidazolyl, etc.

As used herein, the term "hydrocarbyl" has the broadest meaning generally understood in the art, and may include a moiety composed of carbon and hydrogen. Some examples may include alkyl, alkenyl, alkynyl, aryl, etc., and combinations thereof, and may be linear, branched, cyclic, or a combination thereof. Hydrocarbyl may be bonded to any other number of moieties (e.g. be bonded to 1 other group, such as —$CH_3$, —CH=$CH_2$, etc.; 2 other groups, such as -phenyl-, —C≡C—, etc.; or any number of other groups) that the structure may bear, and in some embodiments, may contain from one to thirty-five carbon atoms. Examples of hydrocarbyl groups include but are not limited to $C_1$ alkyl, $C_2$ alkyl, $C_2$ alkenyl, $C_2$ alkynyl, $C_3$ alkyl, $C_3$ alkenyl, $C_3$ alkynyl, $C_4$ alkyl, $C_4$ alkenyl, $C_4$ alkynyl, $C_5$ alkyl, $C_5$ alkenyl, $C_5$ alkynyl, $C_6$ alkyl, $C_6$ alkenyl, $C_6$ alkynyl, phenyl, etc.

Unless otherwise indicated, any reference to a compound or any structural feature herein by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

With respect to any relevant formula or structural depiction herein, such as Formula A, Ph is optionally substituted phenyl. Ph may have 0, 1, 2, 3, or 4 substituents. Any substituent may be included on Ph. In some embodiments, some or all of the substituents on the ring or ring system may have: from 0 to 10 carbon atoms and from 0 to 10 heteroatoms, wherein each heteroatom is independently: O, N, S, F, Cl, Br, or I (provided that there is at least one non-hydrogen atom); and/or a molecular weight of 15 Da to 500 Da. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as optionally substituted methoxy, optionally substituted ethoxy, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$OCOCH_3$, —$CO_2CH_3$, —$OCOC_2H_5$, —$CO_2C_2H_5$, —OCO-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

In some embodiments, Ph may be:

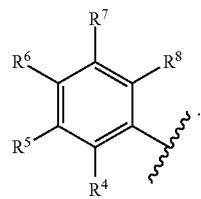

With respect to any relevant formula or structural depiction herein, such as Formula A, Py is optionally substituted pyrrolyl, which may have 0, 1, 2, or 3 substituents. Py may have any suitable substituent. In some embodiments, some or all of the substituents of Py may have: from 0 to 10 carbon atoms and from 0 to 10 heteroatoms, wherein each heteroatom is independently: O, N, S, F, Cl, Br, or I (provided that there is at least one non-hydrogen atom); and/or a molecular weight of 15 Da to 500 Da. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as optionally substituted methoxy, optionally substituted ethoxy, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$OCOCH_3$, —$CO_2CH_3$, —$OCOC_2H_5$, —$CO_2C_2H_5$, —OCO-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

In some embodiments, Py may be:

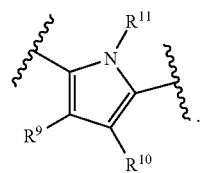

With respect to any relevant formula or structural depiction herein, such as Formula A, $R^1$ can be H; or $C_{1-6}$ hydrocarbyl, such as alkyl (e.g. $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$), alkenyl, (e.g. $C_2H_3$, $C_3H_5$, etc.) alkynyl, (e.g. $C_2H$, $C_2H_3$, etc.), phenyl, etc.

With respect to any relevant formula or structural depiction herein, such as Formula A, A can be H, optionally substituted imidazolyl, optionally substituted thiazolyl, optionally substituted pyrrolyl, morpholine-4-carbonyl, ((2-(methylsulfonamido)ethyl)carbamoyl), optionally substituted piperazin-1-ylcarbamoyl, optionally substituted morpholinocarbamoyl, and/or (2-hydroxyethyl)carbamoyl. A may have any suitable substituent. In some embodiments, some or all of the substituents of A may have: from 0 to 10 carbon atoms and from 0 to 10 heteroatoms, wherein each heteroatom is independently: O, N, S, F, Cl, Br, or I (provided that there is at least one non-hydrogen atom); and/or a molecular weight of 15 Da to 500 Da. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as optionally substituted methoxy, optionally substituted ethoxy, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$OCOCH_3$, —$CO_2CH_3$, —$OCOC_2H_5$, —$CO_2C_2H_5$, —OCO-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

With respect to any relevant formula or structural depiction herein, such as Formula A, B can be optionally substituted aminomethyl; optionally substituted guanidino; optionally substituted guanidino($C_{1-3}$ alkyl), such as optionally substituted guanidinomethyl, optionally substituted guanidinoethyl, optionally substituted guanidinopropyl; optionally substituted phenyl; optionally substituted furanyl; optionally substituted triazolyl; optionally substituted pyrazolyl; and/or optionally substituted phenylmethyl. B may have any suitable substituent. In some embodiments, some or all of the substituents of B may have: from 0 to 10 carbon atoms and from 0 to 10 heteroatoms, wherein each heteroatom is independently: O, N, S, F, Cl, Br, or I (provided that there is at least one non-hydrogen atom); and/or a molecular weight of 15 Da to 500 Da. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as optionally substituted methoxy, optionally substituted ethoxy, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$OCOCH_3$, —$CO_2CH_3$, —$OCOC_2H_5$, —$CO_2C_2H_5$, —OCO-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc.

If stereochemistry is not indicated, such as in Formulas 1-13 and Formula A, a name or structural depiction includes any stereoisomer or any mixture of stereoisomers.

In some embodiments, Formula A may be further described by any of the following Formulas 1-13.

Formula 1
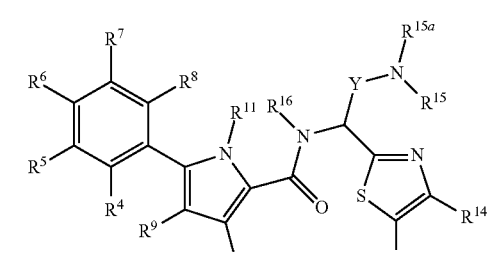
Formula 2
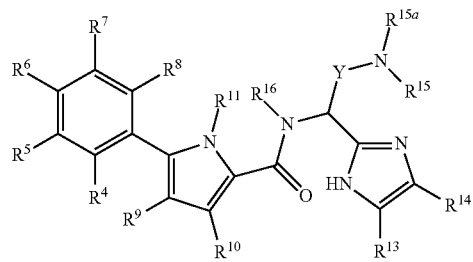
Formula 3
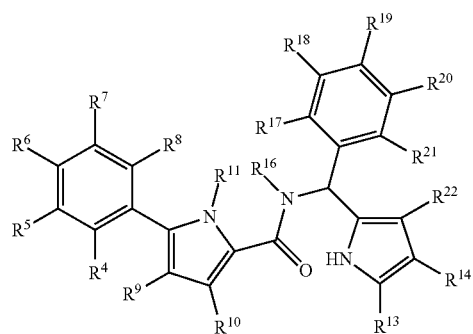
Formula 4
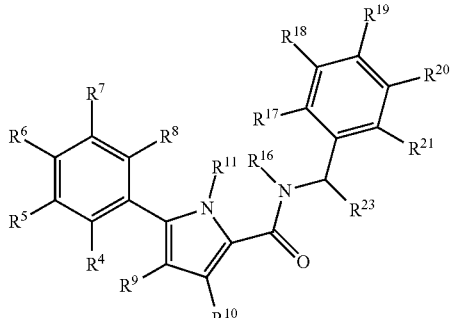
Formula 5
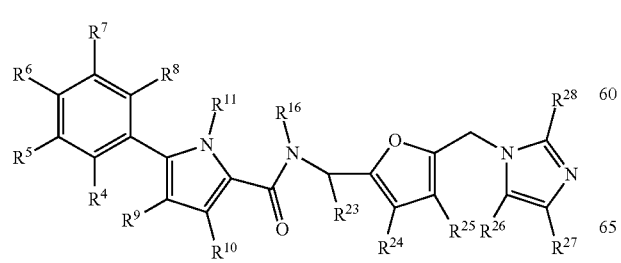
Formula 6
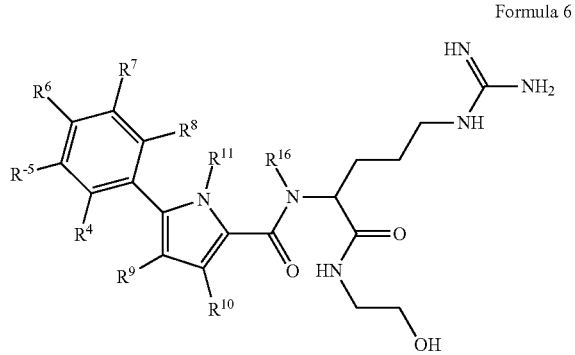
Formula 7
Formula 8
Formula 9
Formula 10
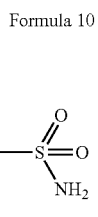

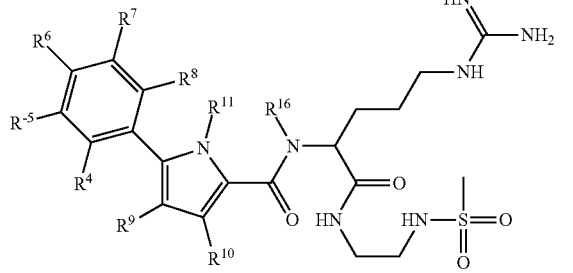

Formula 11

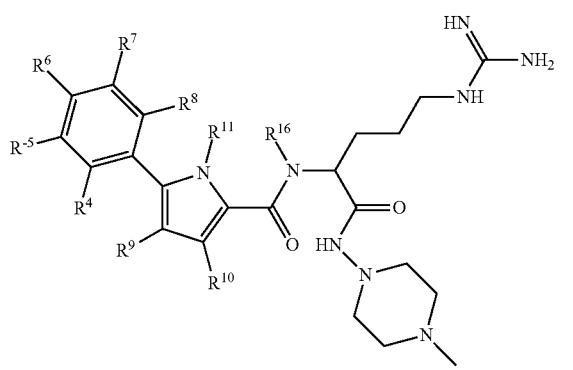

Formula 12

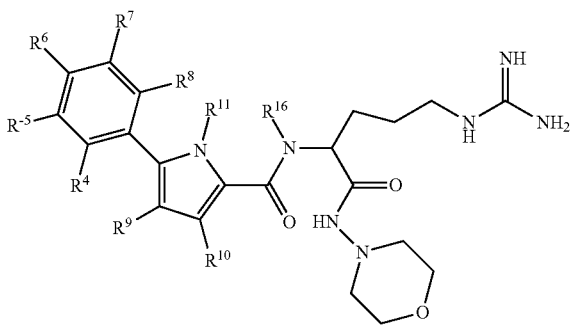

Formula 13

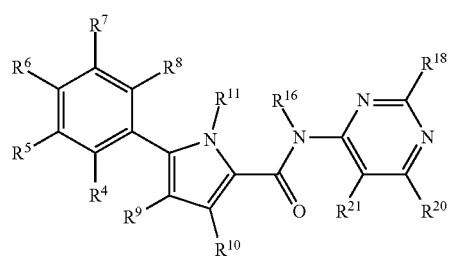

Formula 14

With respect to any relevant structural representation, such as Formulas 1 and 2, in some embodiments, Y is $C_{1-3}$ hydrocarbyl, including $C_{1-3}$ alkyl, such as —$CH_2$—, —$C_2H_4$—, —$C_3H_6$—, etc., or $C_{2-3}$ alkenyl or alkynyl. In some embodiments Y is a bond.

With respect to any relevant structural representation, $R^4$, $R^5$, $R^6$, $R^7$, $R^8$, $R^9$, $R^{10}$, $R^{11}$, $R^{12}$, $R^{13}$, $R^{14}$, $R^{15}$, $R^{15a}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$, may independently be H, a halide, or a substituent having a molecular weight of 15 Da to 300 Da or 15 Da to 150 Da and consisting of 2 to 5 chemical elements, wherein the chemical elements are independently C, H, O, N, S, P, F, Cl, Br, or I. In some embodiments, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are independently $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^4$, $R^5$, $R^6$, $R^7$, $R^8$, $R^9$, $R^{10}$, $R^{11}$, $R^{12}$, $R^{13}$, $R^{14}$, $R^{15}$, $R^{15a}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ are independently H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.

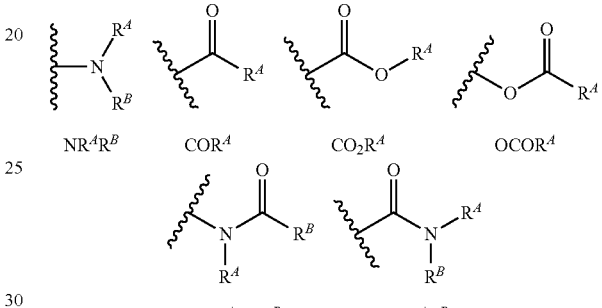

With respect to any relevant structural representation, each $R^A$ may independently be H, or $C_{1-12}$ alkyl, including: linear or branched alkyl having a formula $C_aH_{a+1}$, or cycloalkyl having a formula $C_aH_{a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^A$ may be H or $C_{1-6}$ alkyl. In some embodiments, $R^A$ may be H or $C_{1-3}$ alkyl. In some embodiments, $R^A$ may be H or $CH_3$. In some embodiments, $R^A$ may be H.

With respect to any relevant structural representation, each $R^B$ may independently be H, or $C_{1-12}$ alkyl, including: linear or branched alkyl having a formula $C_aH_{a+1}$; or cycloalkyl having a formula $C_aH_a$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_8H_{17}$, $C_7H_{15}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^B$ may be H or $C_{1-3}$ alkyl. In some embodiments, $R^B$ may be H or $CH_3$. In some embodiments, $R^B$ may be H.

With respect to Formulas 1-14, in some embodiments, $R^4$ is H, F, Cl, $NH_2$, $CH_3$, $SO_2NH_2$, $OCH_3$, $CH_2OH$, $N(C_2H_5)_2$. In some embodiments, $R^4$ is H. Additionally, for any embodiments recited in this paragraph, $R^5$, $R^6$, $R^7$, and $R^8$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-13, in some embodiments, $R^5$ is H, F, Cl, $NH_2$, $CH_3$, $SO_2NH_2$, $OCH_3$, $CH_2OH$, $N(C_2H_5)_2$. In some embodiments, $R^5$ is H. In some embodiments, $R^5$ is F. Additionally, for any embodiments recited in this paragraph, $R^4$, $R^6$, $R^7$, and $R^8$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^6$ is H, F, Cl, $NH_2$, $CH_3$, $SO_2NH_2$, $OCH_3$, $CH_2OH$, $N(C_2H_5)_2$. In some embodiments, $R^6$ is H. In some embodiments, $R^6$ is Cl. In some embodiments, $R^6$ is $CH_3$. Additionally, for any embodiments recited in this paragraph, $R^4$, $R^5$, $R^7$, and $R^8$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^7$ is H, F, Cl, $NH_2$, $CH_3$, $SO_2NH_2$, $OCH_3$, $CH_2OH$, $N(C_2H_5)_2$. In some embodiments, $R^7$ is H. In some embodiments, $R^7$ is F. Additionally, for any embodiments recited in this paragraph, $R^4$, $R^5$, $R^6$, and $R^8$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^8$ is H, F, Cl, $NH_2$, $CH_3$, $SO_2NH_2$, $OCH_3$, $CH_2OH$, $N(C_2H_5)_2$. In some embodiments, $R^8$ is H. Additionally, for any embodiments recited in this paragraph, $R^4$, $R^5$, $R^6$, and $R^7$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-13, in some embodiments, $R^4$ and $R^5$ are H. In some embodiments, $R^5$ and $R^6$ are H. In some embodiments, $R^6$ and $R^7$ are H. In some embodiments, $R^7$ and $R^8$ are H. In some embodiments, $R^4$, $R^5$, $R^6$, $R^7$, and $R^8$ are H.

With respect to Formulas 1-14, in some embodiments, $R^9$ is H, F, Cl, $NH_2$, $CH_3$, $SO_2NH_2$, $OCH_3$, $CH_2OH$, $N(C_2H_5)_2$. In some embodiments, $R^9$ is H. Additionally, for any embodiments recited in this paragraph, $R^{10}$, and $R^{11}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{10}$ is H, F, Cl, $NH_2$, $CH_3$, $SO_2NH_2$, $OCH_3$, $CH_2OH$, $N(C_2H_5)_2$. In some embodiments, $R^{10}$ is H. Additionally, for any embodiments recited in this paragraph, $R^9$, and $R^{11}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{11}$ is H, F, Cl, $NH_2$, $CH_3$, $SO_2NH_2$, $OCH_3$, $CH_2OH$, $N(C_2H_5)_2$. In some embodiments, $R^{11}$ is H. Additionally, for any embodiments recited in this paragraph, $R^9$, and $R^{10}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{12}$ is H, F, Cl, $NH_2$, $CH_3$, $SO_2NH_2$, $OCH_3$, $CH_2OH$, $N(C_2H_5)_2$. In some embodiments, $R^{12}$ is H. Additionally, for any embodiments recited in this paragraph, $R^{15}$ and $R^{16}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{13}$ is H, F, Cl, $NH_2$, $CH_3$, $SO_2NH_2$, $OCH_3$, $CH_2OH$, $N(C_2H_5)_2$. In some embodiments, $R^{13}$ is H. In some embodiments, $R^{13}$ is —$CH_2OH$. Additionally, for any embodiments recited in this paragraph, $R^{14}$ and $R^{22}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{14}$ is H, F, Cl, $NH_2$, $CH_3$, $SO_2NH_2$, $OCH_3$, $CH_2OH$, $N(C_2H_5)_2$. In some embodiments, $R^{14}$ is H. In some embodiments, $R^{14}$ is $CH_3$. Additionally, for any embodiments recited in this paragraph, $R^{13}$ and $R^{22}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{15}$ is H, F, Cl, $NH_2$, $CH_3$, $SO_2NH_2$, $OCH_3$, $CH_2OH$, $N(C_2H_5)_2$. In some embodiments, $R^{15}$ is H. In some embodiments, $R^{15}$ and $R^{15a}$ may together form a ring, such as, but not limited to piperidinyl. In some embodiments, $R^{15}$ is $CH_3$. In some embodiments, $R^{15}$ is acetyl. In some embodiments, $R^{15}$ is carbamimidoyl. Additionally, for any embodiments recited in this paragraph, $R^{12}$, $R^{15a}$, and $R^{16}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{15a}$ is H, F, Cl, $NH_2$, $CH_3$, $SO_2NH_2$, $OCH_3$, $CH_2OH$, $N(C_2H_5)_2$. In some embodiments, $R^{15a}$ is H. In some embodiments, $R^{15a}$ and $R^{15a}$ may together form a ring, such as, but not limited to piperidinyl. In some embodiments, $R^{15}$ is $CH_3$. In some embodiments, $R^{15a}$ is acetyl. In some embodiments, $R^{15}$ is carbamimidoyl. Additionally, for any embodiments recited in this paragraph, $R^{12}$, $R^{15}$, and $R^{16}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{16}$ is H, F, Cl, $NH_2$, $CH_3$, $SO_2NH_2$, $OCH_3$, $CH_2OH$, $N(C_2H_5)_2$. In some embodiments, $R^{16}$ is H. Additionally, for any embodiments recited in this paragraph, $R^{12}$, $R^{15}$ and, where applicable, $R^{23}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{17}$ is H, F, Cl, $NH_2$, $CH_3$, $SO_2NH_2$, $OCH_3$, $CH_2OH$, $N(C_2H_5)_2$. In some embodiments, $R^{17}$ is H. In some embodiments, $R^{17}$ is methoxy. Additionally, for any embodiments recited in this paragraph, $R^{18}$, $R^{19}$, $R^{20}$, and $R^{21}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{18}$ is H, F, Cl, $NH_2$, $CH_3$, $SO_2NH_2$, $OCH_3$, $CH_2OH$, $N(C_2H_5)_2$. In some embodiments, $R^{18}$ is H. In some embodiments, $R^{18}$ is guanidino. In some embodiments, $R^{18}$ is (diethylamino)methyl. Additionally, for any embodiments recited in this paragraph, $R^{17}$, $R^{19}$, $R^{20}$, and $R^{21}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{19}$ is H, F, Cl, $NH_2$, $CH_3$, $SO_2NH_2$, $OCH_3$, $CH_2OH$, $N(C_2H_5)_2$. In some embodiments, $R^{19}$ is H. Additionally, for any embodiments recited in this paragraph, $R^{17}$, $R^{18}$, $R^{20}$, and $R^{21}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{20}$ is H, F, Cl, $NH_2$, $CH_3$, $SO_2NH_2$, $OCH_3$, $CH_2OH$, $N(C_2H_5)_2$. In some embodiments, $R^{20}$ is H. In some embodiments, $R^{20}$ is methylamino. In some embodiments, $R^{20}$ is (diethylamino)methyl. In some embodiments, $R^{20}$ is $SO_2NH_2$. Additionally, for any embodiments recited in this paragraph, $R^{17}$, $R^{18}$, $R^{19}$, and $R^{21}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{21}$ is H, F, Cl, $NH_2$, $CH_3$, $SO_2NH_2$, $OCH_3$, $CH_2OH$, $N(C_2H_5)_2$. In some embodiments, $R^{21}$ is H. In some embodiments, $R^{21}$ is methoxy. Additionally, for any embodiments recited in this paragraph, $R^{17}$, $R^{18}$, $R^{19}$, and $R^{20}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{22}$ is H, F, Cl, $NH_2$, $CH_3$, $SO_2NH_2$, $OCH_3$, $CH_2OH$, $N(C_2H_5)_2$. In some embodiments, $R^{22}$ is H. Additionally, for any embodiments recited in this paragraph, $R^{13}$ and $R^{14}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{23}$ is H, F, Cl, $NH_2$, $CH_3$, $SO_2NH_2$, $OCH_3$, $CH_2OH$, $N(C_2H_5)_2$. In some embodiments, $R^{23}$ is H. Additionally, for any embodiments recited in this paragraph, $R^{16}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{24}$ is H, F, Cl, $NH_2$, $CH_3$, $SO_2NH_2$, $OCH_3$, $CH_2OH$, $N(C_2H_5)_2$. In some embodiments, $R^{24}$ is H. Additionally, for any embodiments recited in this paragraph, $R^{25}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{25}$ is H, F, Cl, $NH_2$, $CH_3$, $SO_2NH_2$, $OCH_3$, $CH_2OH$, $N(C_2H_5)_2$. In some embodiments, $R^{25}$ is H. Additionally, for any embodiments recited in this paragraph, $R^{24}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{26}$ is H, F, Cl, $NH_2$, $CH_3$, $SO_2NH_2$, $OCH_3$, $CH_2OH$, $N(C_2H_5)_2$. In some embodiments, $R^{26}$ is H. In some embodiments, $R^{26}$ is $NH_2$. Additionally, for any embodiments recited in this paragraph, $R^{27}$ and $R^{28}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{27}$ is H, F, Cl, $NH_2$, $CH_3$, $SO_2NH_2$, $OCH_3$, $CH_2OH$, $N(C_2H_5)_2$. In some embodiments, $R^{27}$ is H. Additionally, for any embodiments recited in this paragraph, $R^{26}$ and $R^{28}$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

With respect to Formulas 1-14, in some embodiments, $R^{28}$ is H, F, Cl, $NH_2$, $CH_3$, $SO_2NH_2$, $OCH_3$, $CH_2OH$, $N(C_2H_5)_2$. In some embodiments, $R^{28}$ is H. In some embodiments, $R^{28}$ is $CH_3$. Additionally, for any embodiments recited in this paragraph, $R^{26}$ and $R^{27}$ can be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

In some embodiments, a compound of Formula 1 can be:

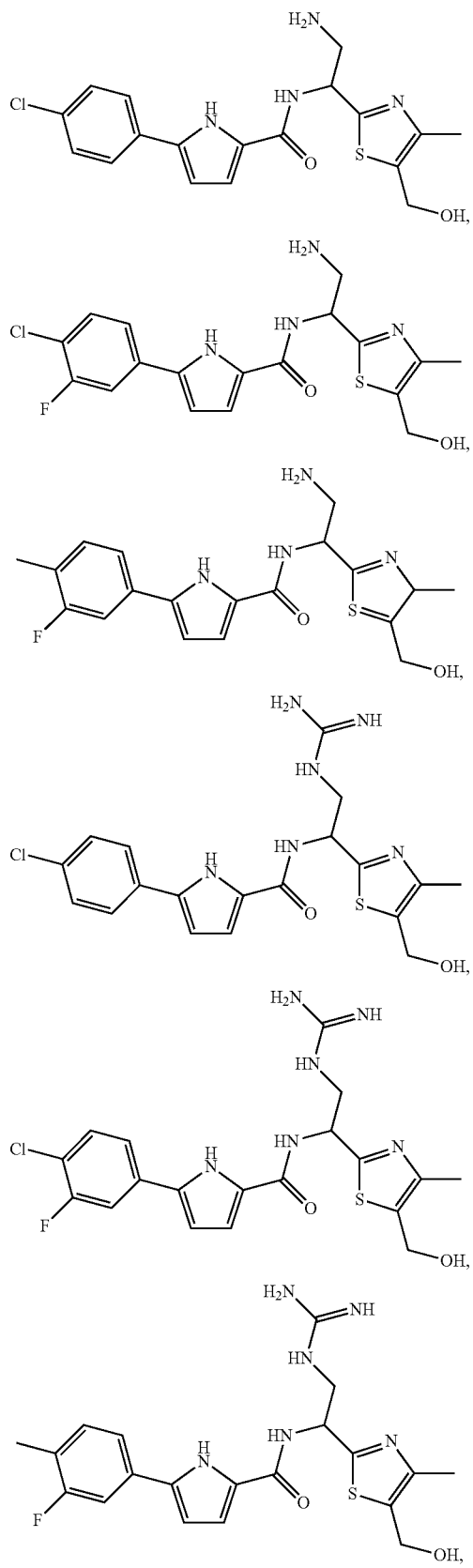

-continued
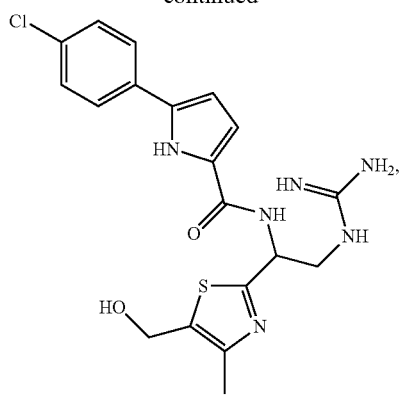
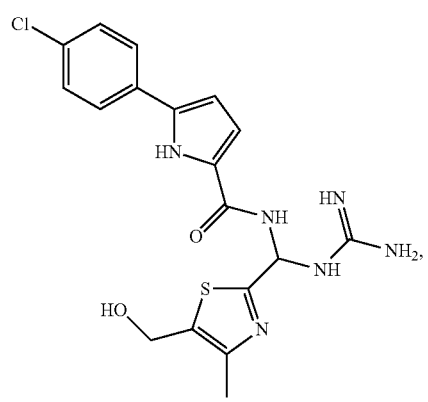
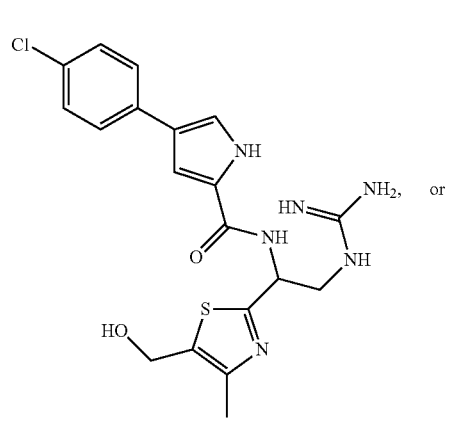
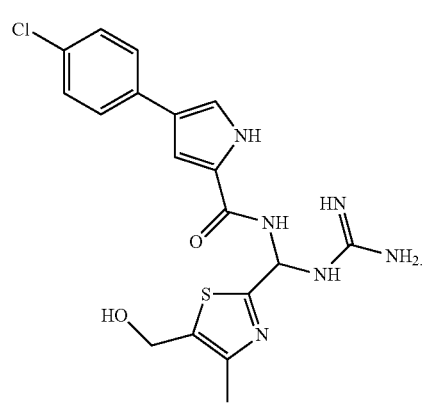
In some embodiments, a compound of Formula 2 can be:
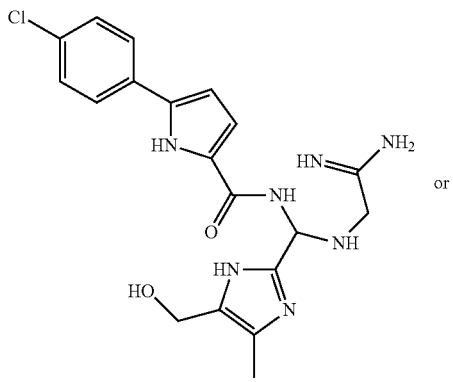
or
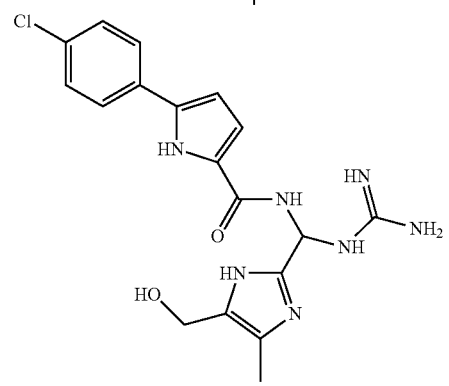
In some embodiments, a compound of Formula 3 can be:
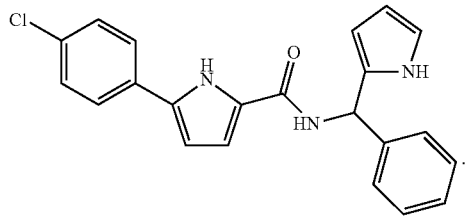 [SMILES: O=C(NC(c1ccccc1)c1ccc[nH]1)c1ccc(-c2ccc(Cl)cc2)[nH]1]
In some embodiments, a compound of Formula 4 can be:
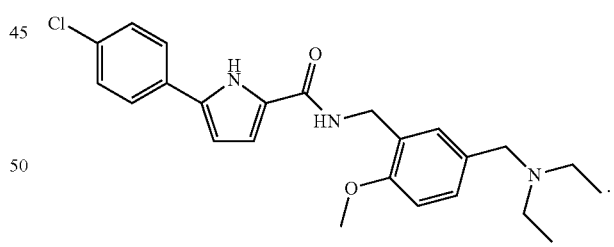
In some embodiments, a compound of Formula 5 can be:
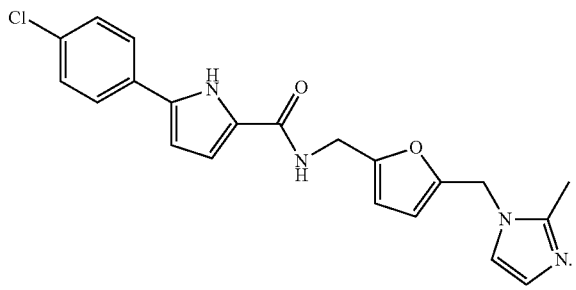 [SMILES: Cc1nccn1Cc1ccc(CNC(=O)c2ccc(-c3ccc(Cl)cc3)[nH]2)o1]

In some embodiments, a compound of Formula 6 can be:
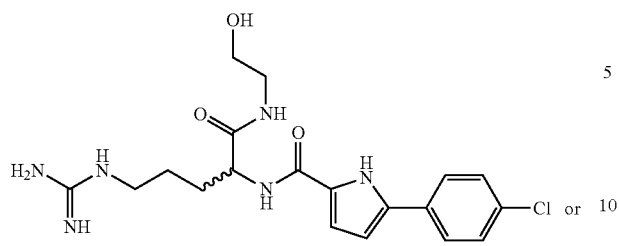
or
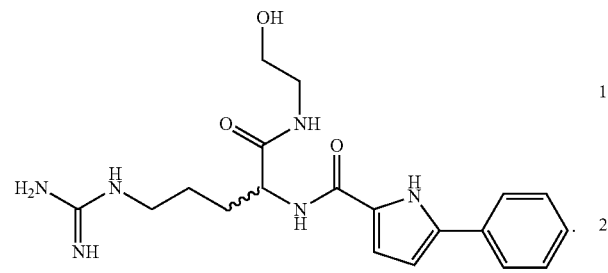
In some embodiments, a compound of Formula 7 can be:
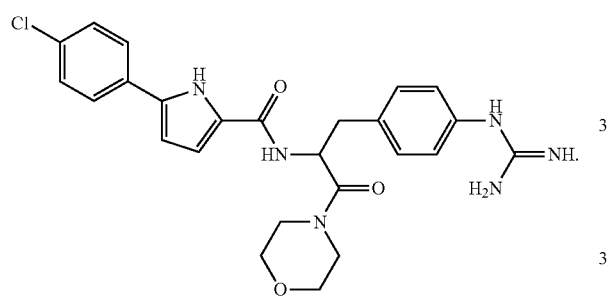
In some embodiments, a compound of Formula 8 can be:
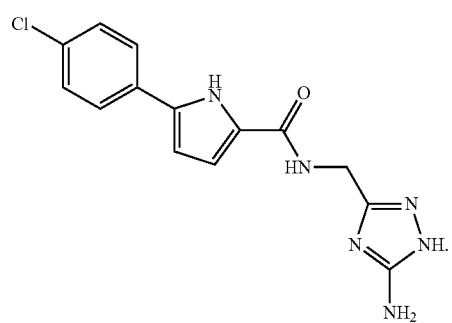 [SMILES: Nc1nc(CNC(=O)c2ccc(-c3ccc(Cl)cc3)[nH]2)n[nH]1]
In some embodiments, a compound of Formula 9 can be:
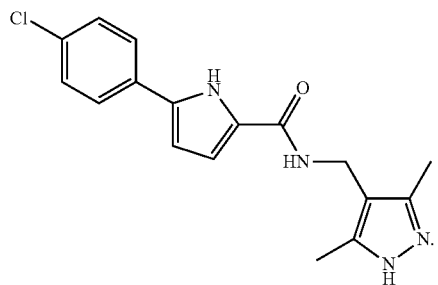
In some embodiments, a compound of Formula 10 can be:
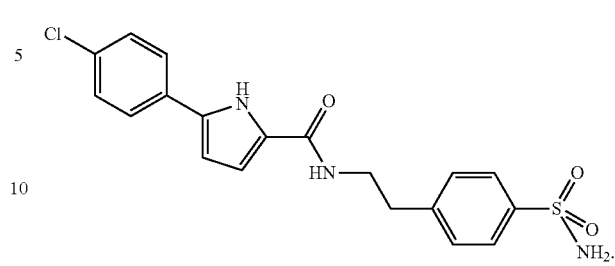
In some embodiments, a compound of Formula 11 can be:
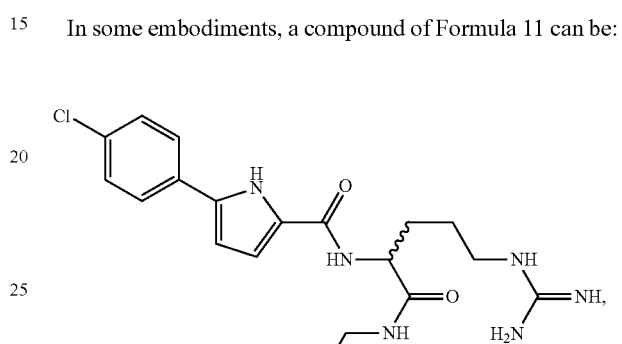
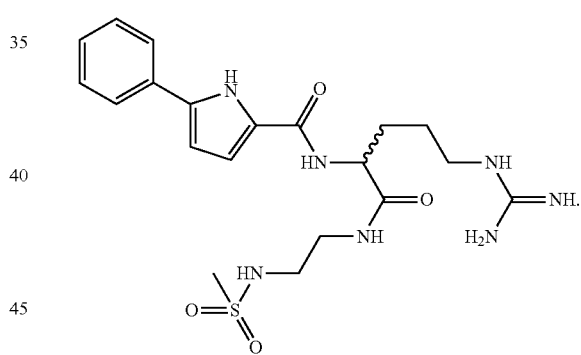
In some embodiments, a compound of Formula 12 can be:
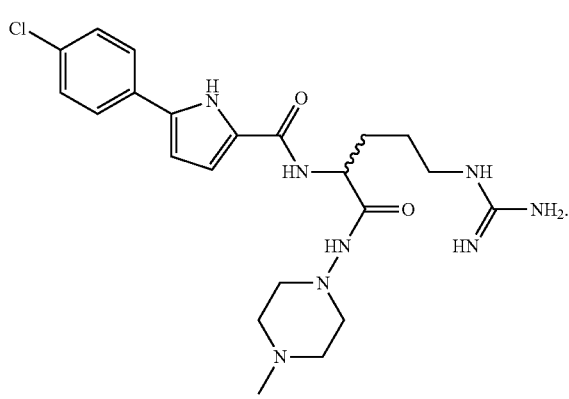 [SMILES: CN1CCN(NC(=O)C(CCCNC(=N)N)NC(=O)c2ccc(-c3ccc(Cl)cc3)[nH]2)CC1]

In some embodiments, a compound of Formula 13 can be:

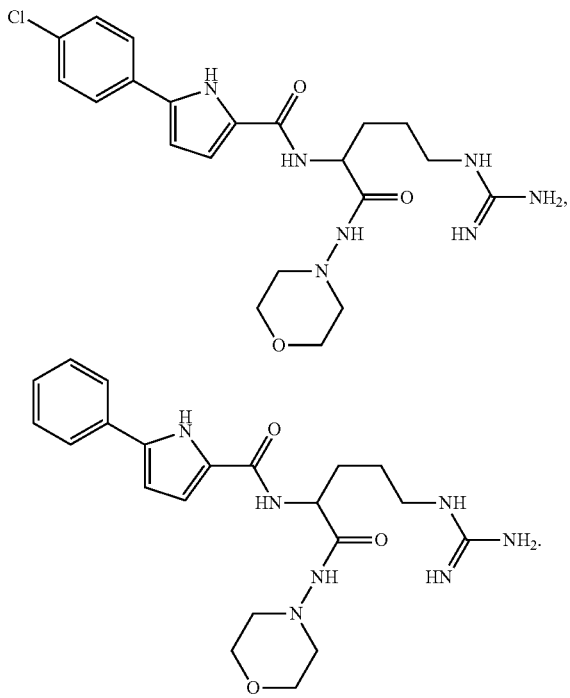

The compounds described herein, such as compounds of Formulas A and 1-13 (referred to hereafter as "subject compounds" or "subject compound") may be used as inhibitors of human immunodeficiency virus (HIV) and/or for treating associated diseases, disorders, and conditions. A pharmaceutical composition comprising at least one subject compound may be administered to individuals suffering from or susceptible to HIV-1 infection.

Appropriate excipients for use in a pharmaceutical composition comprising a subject compound (referred to hereafter as "subject compositions" or "subject composition") may include, for example, one or more carriers, binders, fillers, vehicles, disintegrants, surfactants, dispersion or suspension aids, thickening or emulsifying agents, isotonic agents, preservatives, lubricants, and the like or combinations thereof, as suited to a particular dosage from desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. This document is incorporated herein by reference in its entirety.

A subject composition may be formulated for any desirable route of delivery including, but not limited to, parenteral, intravenous, intradermal, subcutaneous, oral, inhalative, transdermal, topical, transmucosal, rectal, interacisternal, intravaginal, intraperitoneal, buccal, and intraocular.

In certain aspects, parenteral, intradermal or subcutaneous formulations may be sterile injectable aqueous or oleaginous suspensions. Acceptable vehicles, solutions, suspensions and solvents may include, but are not limited to, water or other sterile diluent; saline; Ringer's solution; sodium chloride; fixed oils such as mono- or diglycerides; fatty acids such as oleic acid; polyethylene glycols; glycerine; propylene glycol or other synthetic solvents; antibacterial agents such as benzyl alcohol; antioxidants such as ascorbic acid; chelating agents such as ethylenediaminetetraacetic acid; buffers such as acetates, citrates or phosphates; and agents for the adjustment of tonicity such as sodium chloride or dextrose.

Solutions or suspensions used for parenteral, intradermal, or subcutaneous application may include one or more of the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation may be enclosed in ampoules, disposable syringes or multiple dose vials made of glass or plastic.

Pharmaceutical compositions suitable for injectable use may include sterile aqueous solutions or dispersions and sterile powders for the extemporaneous preparation of sterile injectable solutions or dispersion. For intravenous administration, suitable carriers include, but are not limited to, saline, bacteriostatic water, CREMOPHOR EL® (BASF, Parsippany, N.J.) or phosphate buffered saline (PBS). The solvent or dispersion medium may contain, for example, water, ethanol, polyol (for example, glycerol, propylene glycol, and liquid polyethylene glycol, and the like), and suitable mixtures thereof. Proper fluidity can be maintained, for example, by the use of a coating such as lecithin, by the maintenance of the required particle size in the case of dispersion and by the use of surfactants. Preventing growth of microorganisms can be achieved by various antibacterial and antifungal agents, for example, parabens, chlorobutanol, phenol, ascorbic acid, thimerosal, and the like. The composition may also include isotonic agents such as, for example, sugars; polyalcohols such as manitol; sorbitol; or sodium chloride. Prolonged absorption of injectable compositions can be enhanced by addition of an agent that delays absorption, such as, for example, aluminum monostearate or gelatin.

Oral compositions may include an inert diluent or an edible carrier. They may be enclosed in gelatin capsules or compressed into tablets. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

In addition to oral or injected administration, systemic administration may be by transmucosal or transdermal means. For transmucosal or transdermal administration, penetrants may be used. Such penetrants are generally known in the art, and include, for example, detergents, bile salts, and fusidic acid derivatives. Transdermal administration may include a bioactive agent and may be formulated into ointments, salves, gels, or creams as generally known in the art. Transmucosal administration may be accomplished through the use of nasal sprays or suppositories.

A subject compound may be administered in a therapeutically effective amount, according to an appropriate dosing regiment. As understood by a skilled artisan, an exact amount required may vary from subject to subject, depending on a subject's species, age and general condition, the severity of the infection, the particular agent(s) and the mode of administration. In some embodiments, about 0.001 mg/kg to about 50 mg/kg, of the pharmaceutical composition based on the subject's body weight is administered, one or more times a day, to obtain the desired therapeutic effect. In other embodiments, about 0.01 mg/kg to about 25 mg/kg, of the pharmaceutical composition based on the subject's body weight is administered, one or more times a day, to obtain the desired therapeutic effect.

A total daily dosage of a subject compound can be determined by the attending physician within the scope of sound medical judgment. A specific therapeutically effective dose level for any particular patient or subject will depend upon a variety of factors including the disorder being treated and the severity of the disorder; the activity of the specific compound employed; the specific composition employed; the age, body weight, general health, sex and diet of the patient or subject; the time of administration, route of administration, and rate of excretion of the specific compound employed; the duration of the treatment; drugs used in combination or coincidental with the specific compound employed; and other factors well known in the medical arts.

Although there are many ways in which Formula A might be prepared, Formula A can be synthesized by a peptide coupling reaction, as follows, which couples Precursor 1 with Intermediate 1 to form Formula A.

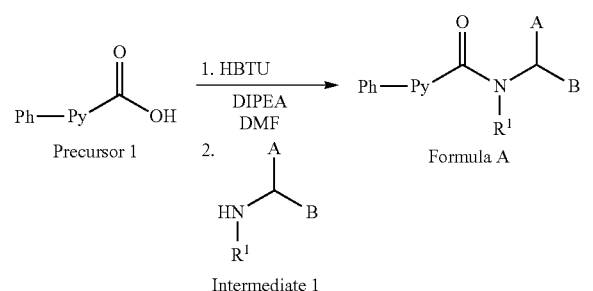

In some embodiments Intermediate 1 is pretreated with tetraphenylborate before the peptide coupling reaction is carried out to avoid unintended coupling of amino substituents (see U.S. Pat. No. 5,262,567).

Although there are many ways that Intermediate 1 can be prepared, Intermediate 1, having a structure

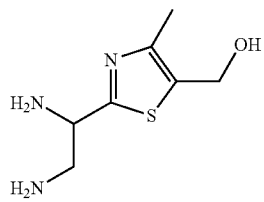

can be prepared as shown in Scheme 1.

Scheme 1

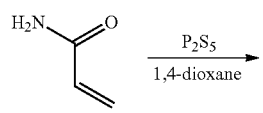

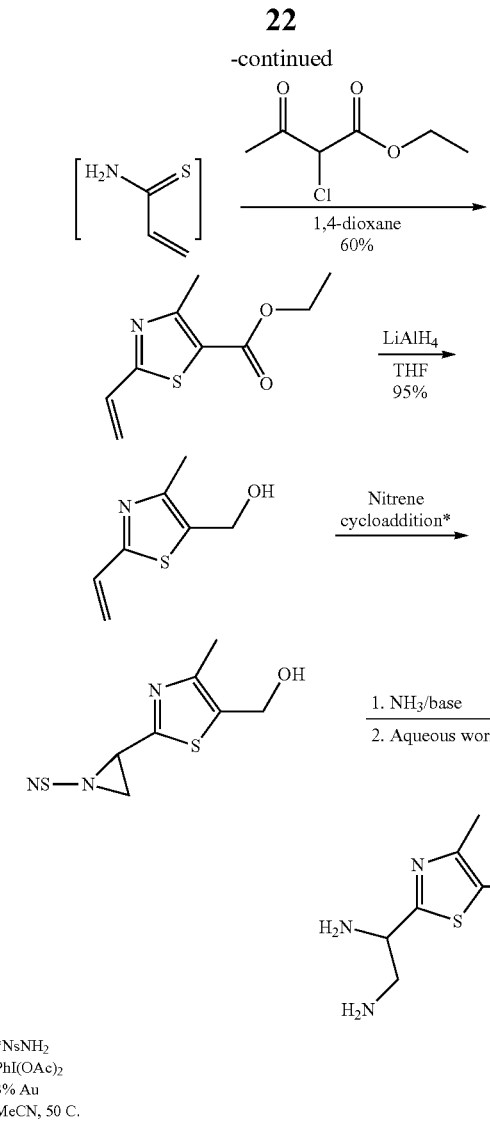

*NsNH$_2$
PhI(OAc)$_2$
3% Au
MeCN, 50 C.

Although there are many ways that Intermediate 1 can be prepared, Intermediate 1, having a structure

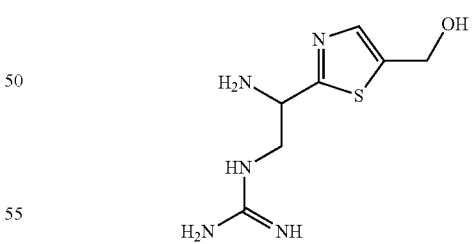

can be prepared as shown in Scheme 2.

Scheme 2

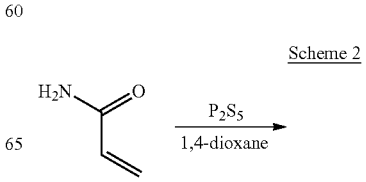

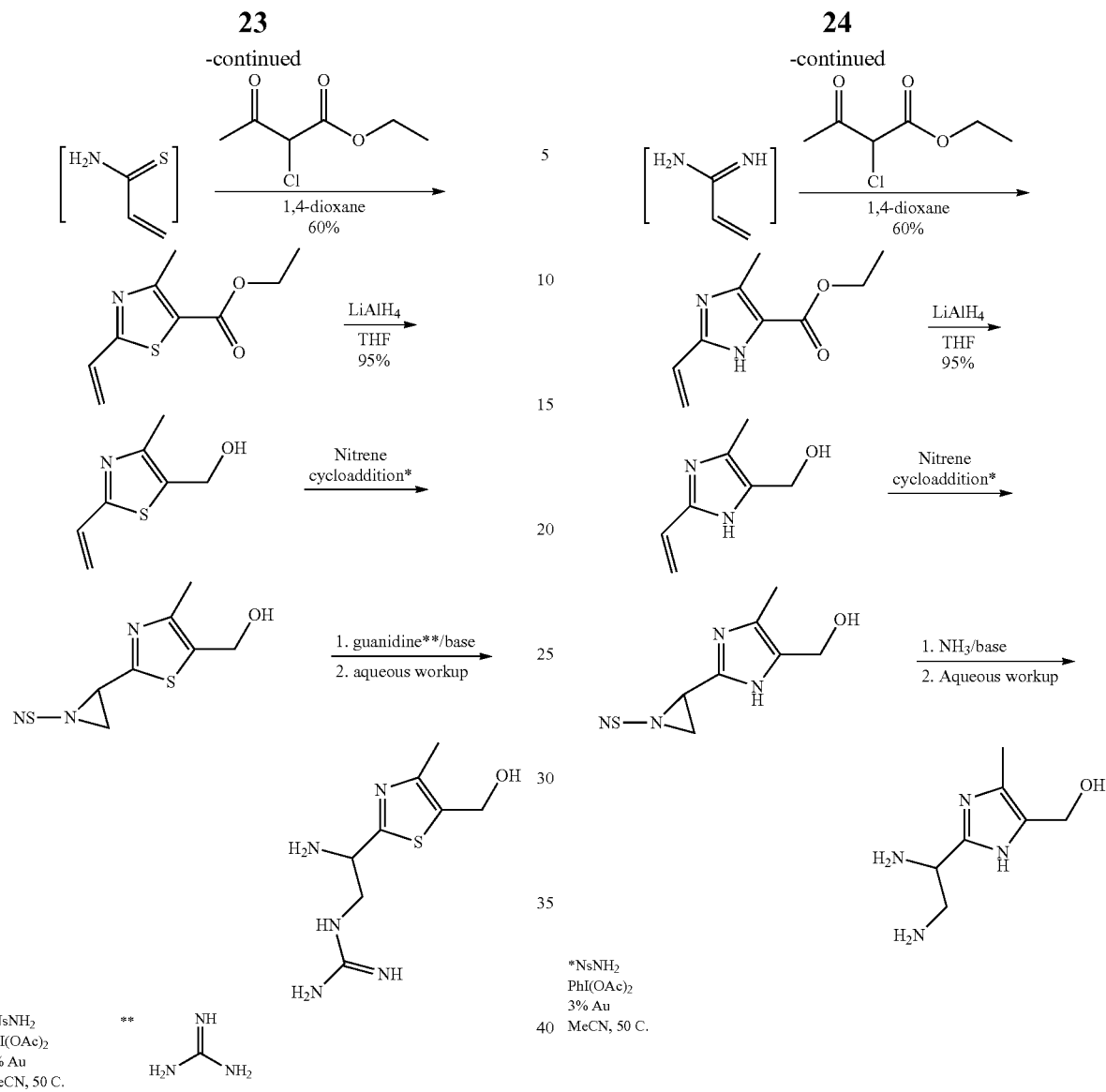
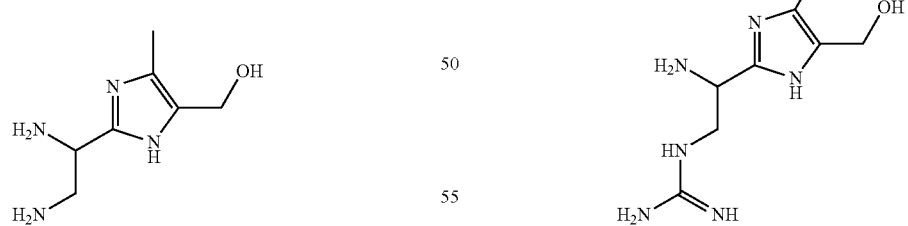
Although there are many ways that Intermediate 1 can be prepared, Intermediate 1, having a structure
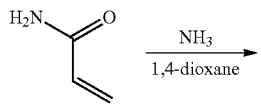
can be prepared as shown in Scheme 3.
Although there are many ways that Intermediate 1 can be prepared, Intermediate 1, having a structure
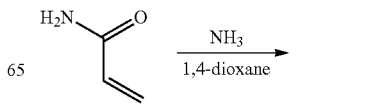
can be prepared as shown in Scheme 4.

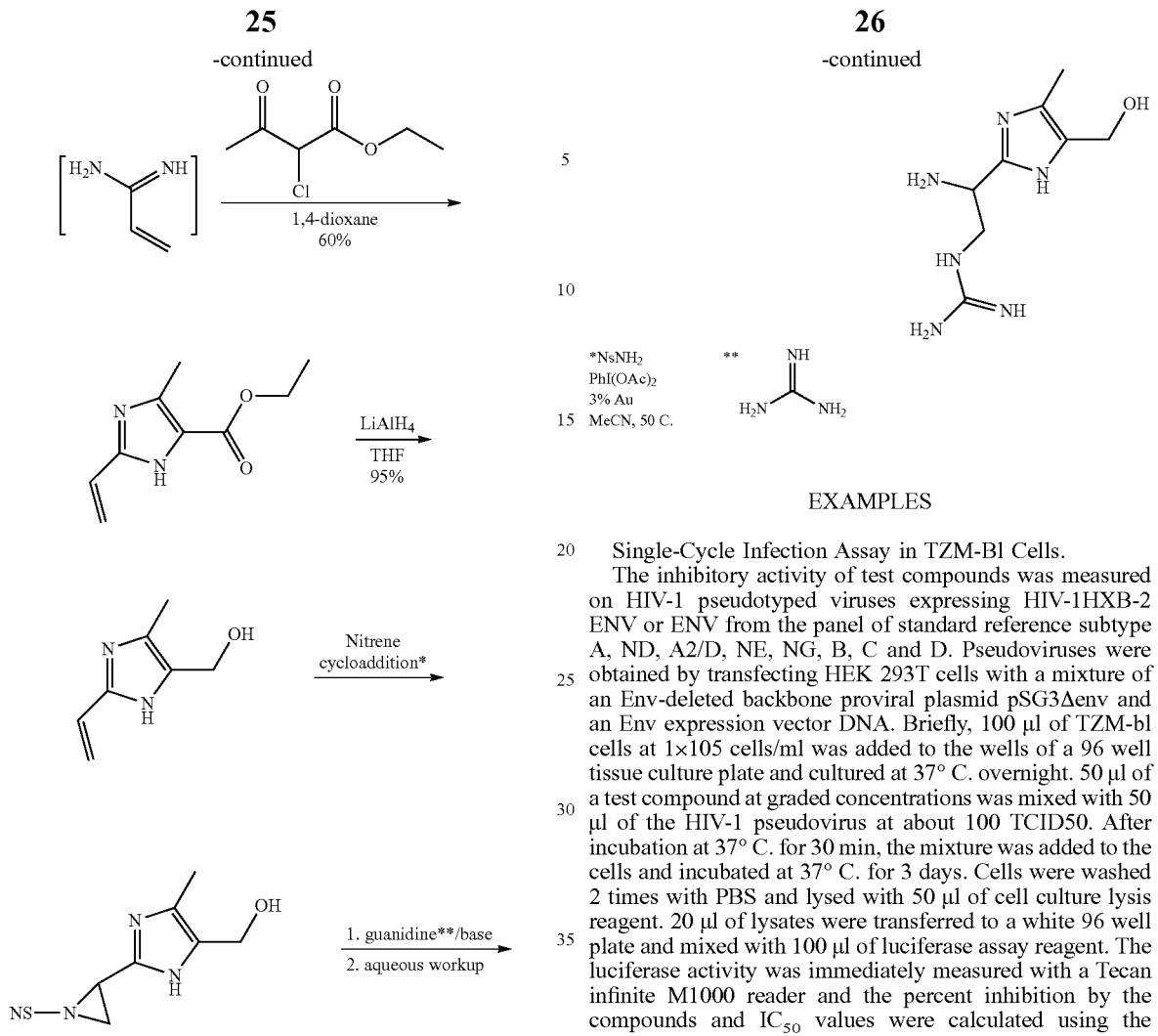

EXAMPLES

Single-Cycle Infection Assay in TZM-Bl Cells.

The inhibitory activity of test compounds was measured on HIV-1 pseudotyped viruses expressing HIV-1HXB-2 ENV or ENV from the panel of standard reference subtype A, ND, A2/D, NE, NG, B, C and D. Pseudoviruses were obtained by transfecting HEK 293T cells with a mixture of an Env-deleted backbone proviral plasmid pSG3Δenv and an Env expression vector DNA. Briefly, 100 μl of TZM-bl cells at 1×105 cells/ml was added to the wells of a 96 well tissue culture plate and cultured at 37° C. overnight. 50 μl of a test compound at graded concentrations was mixed with 50 μl of the HIV-1 pseudovirus at about 100 TCID50. After incubation at 37° C. for 30 min, the mixture was added to the cells and incubated at 37° C. for 3 days. Cells were washed 2 times with PBS and lysed with 50 μl of cell culture lysis reagent. 20 μl of lysates were transferred to a white 96 well plate and mixed with 100 μl of luciferase assay reagent. The luciferase activity was immediately measured with a Tecan infinite M1000 reader and the percent inhibition by the compounds and $IC_{50}$ values were calculated using the GraphPad Prism software. (see Table 1 & 2)

TABLE 1

Antiviral activity of small molecules in single cycle assy, TZM-bl cells infected with HIV-1 pseudovirus pseudotyped with HXB2 Env.

| Compound Number | Structure | TZM-bl | |
|---|---|---|---|
| | | $IC_{50}$ (μM) | CC (μM) |
| 1 | | 16.4 ± 1.5 | >53 |

TABLE 1-continued
Antiviral activity of small molecules in single cycle assy, TZM-bl cells infected with HIV-1 pseudovirus pseudotyped with HXB2 Env.
| Compound Number | Structure | TZM-bl IC$_{50}$ (μM) | CC (μM) |
|---|---|---|---|
| 2 | 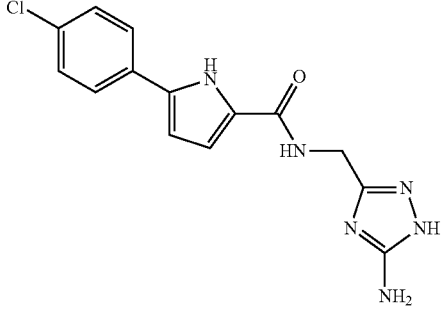 [SMILES: Nc1nc(CNC(=O)c2ccc(-c3ccc(Cl)cc3)[nH]2)n[nH]1] | >63 | >63 |
| 3 | 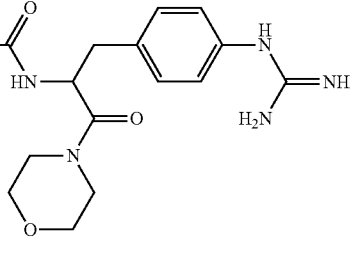 | >36 | >36 |
| 4 | 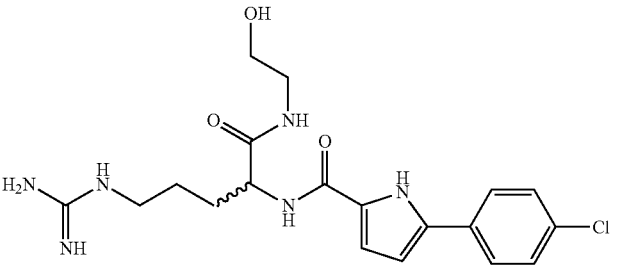 [SMILES: N=C(N)NCCCC(NC(=O)c1ccc(-c2ccc(Cl)cc2)[nH]1)C(=O)NCCO] | >44 | >44 |
| 5 | 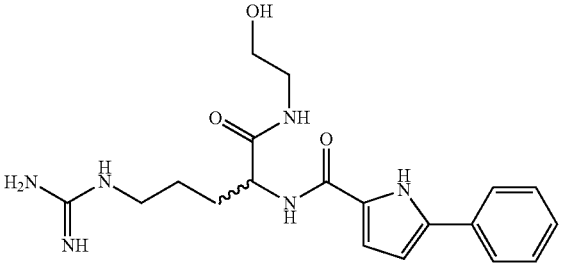 [SMILES: N=C(N)NCCCC(NC(=O)c1ccc(-c2ccccc2)[nH]1)C(=O)NCCO] | >47 | >47 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (µM) | CC (µM) |
|---|---|---|---|
| 6 | 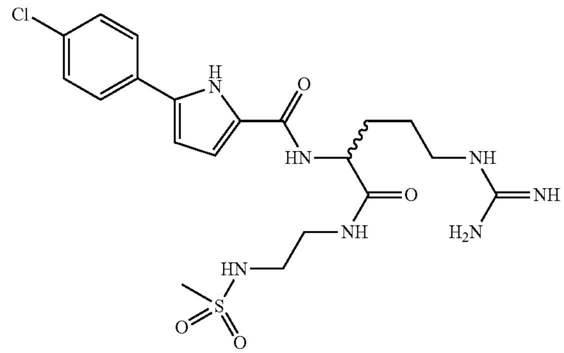 [SMILES: CS(=O)(=O)NCCNC(=O)C(CCCNC(=N)N)NC(=O)c1ccc(-c2ccc(Cl)cc2)[nH]1] | >37 | >37 |
| 7 | 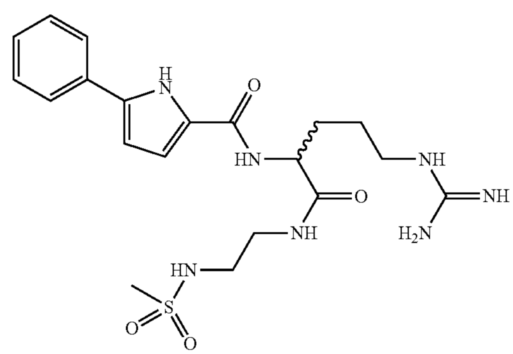 [SMILES: CS(=O)(=O)NCCNC(=O)C(CCCNC(=N)N)NC(=O)c1ccc(-c2ccccc2)[nH]1] | >43 | >43 |
| 8 | 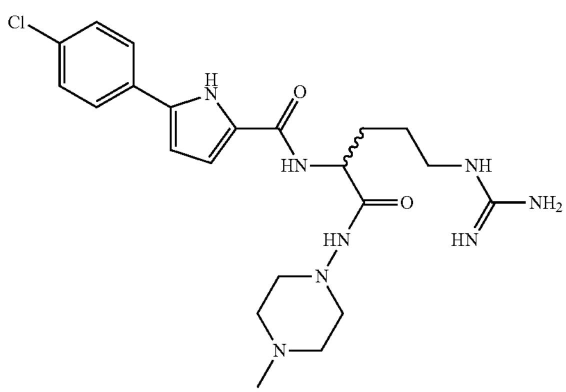 [SMILES: CN1CCN(NC(=O)C(CCCNC(=N)N)NC(=O)c2ccc(-c3ccc(Cl)cc3)[nH]2)CC1] | >42 | >42 |
| 9 | 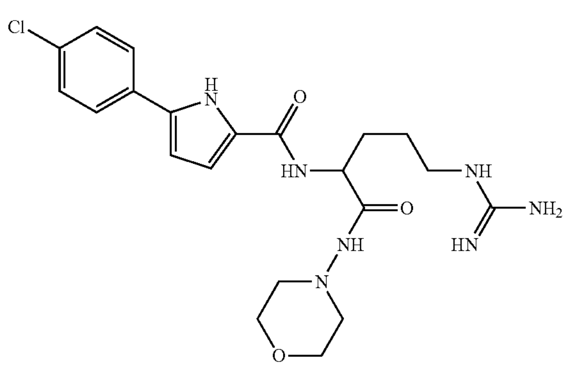 [SMILES: N=C(N)NCCCC(NC(=O)c1ccc(-c2ccc(Cl)cc2)[nH]1)C(=O)NN1CCOCC1] | >40 | >40 |

TABLE 1-continued
Antiviral activity of small molecules in single cycle assy, TZM-bl cells infected with HIV-1 pseudovirus pseudotyped with HXB2 Env.
| Compound Number | Structure | TZM-bl IC$_{50}$ (μM) | CC (μM) |
|---|---|---|---|
| 10 | 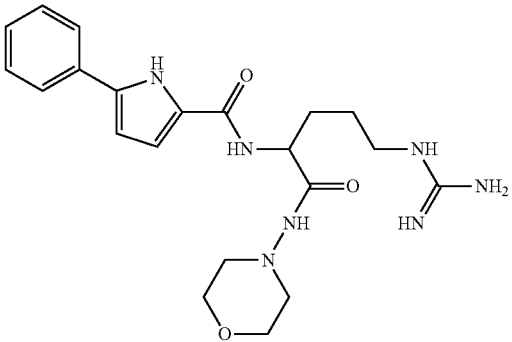 [SMILES: N=C(N)NCCCC(NC(=O)c1ccc(-c2ccccc2)[nH]1)C(=O)NN1CCOCC1] | >43 | >43 |
| 11 | 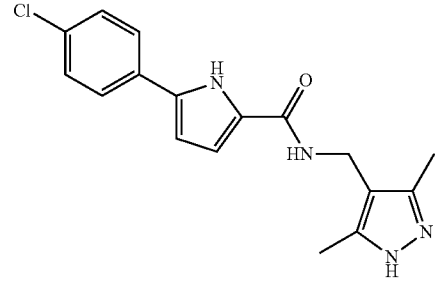 [SMILES: Cc1n[nH]c(C)c1CNC(=O)c1ccc(-c2ccc(Cl)cc2)[nH]1] | ~60 | ~60 |
| 12 | 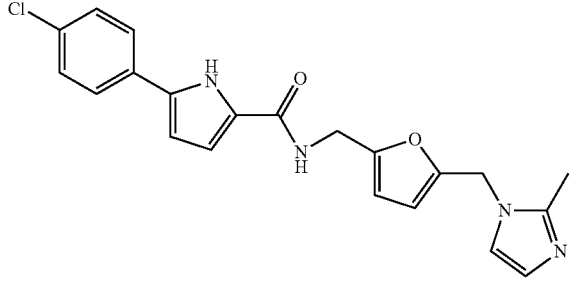 [SMILES: Cc1nccn1Cc1ccc(CNC(=O)c2ccc(-c3ccc(Cl)cc3)[nH]2)o1] | 14.1 ± 1.3 | 22 ± 0.4 |
| 13 | 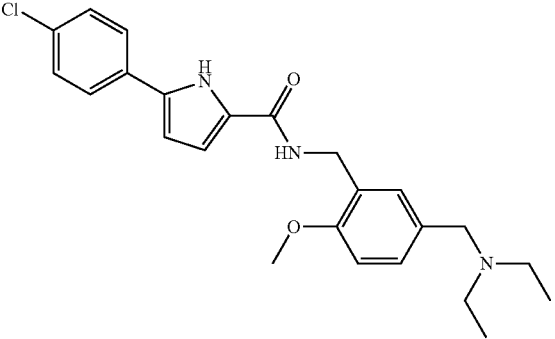 [SMILES: CCN(CC)Cc1ccc(OC)c(CNC(=O)c2ccc(-c3ccc(Cl)cc3)[nH]2)c1] | 4.3 ± 0.1 | 14.2 ± 1 |

TABLE 1-continued
Antiviral activity of small molecules in single cycle assy, TZM-bl cells infected with HIV-1 pseudovirus pseudotyped with HXB2 Env.
| Compound Number | Structure | TZM-bl IC$_{50}$ (μM) | CC (μM) |
|---|---|---|---|
| 14 | 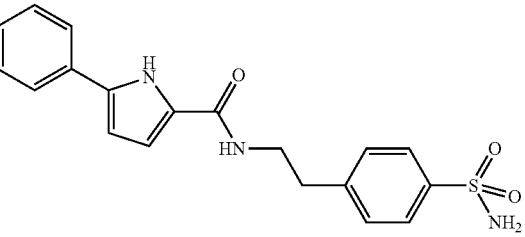 | >50 | >50 |
| 15 | 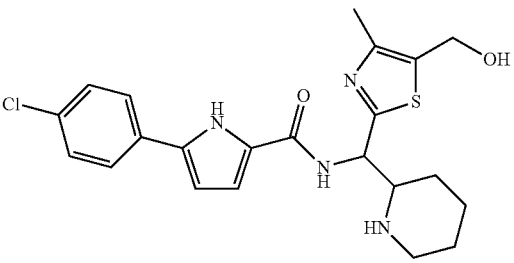<br>Diastereoisomeric mixtures | 2.5 ± 0.2 | ~28 |
| 16 | 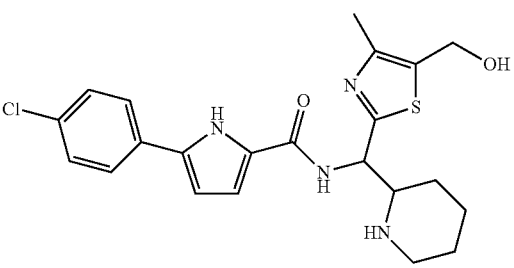<br>Stereoisomer 1 | 3.2 ± 0.3 | ~30 |
| 17 | 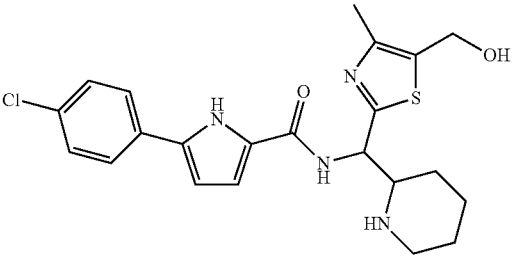<br>Stereoisomer 2 | 2.2 ± 0.2 | ~24 |
| 18 | 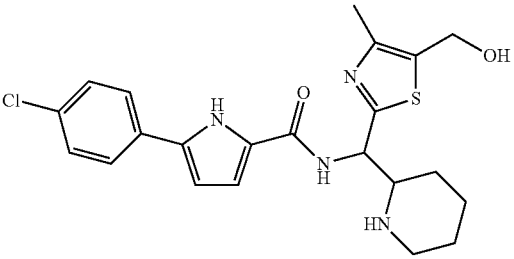<br>Stereoisomer 3 | 3.0 ± 0.1 | ~28 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC₅₀ (μM) | CC (μM) |
|---|---|---|---|
| 19 | Stereoisomer 4 | 0.99 ± 0.13 | ~24 |
| 20 | Diastereoisomer 1 | 3 ± 0.4 | 15.2 ± 0.2 |
| 21 | Diastereoisomer 2 | 3.2 ± 0.5 | 17.4 ± 1.6 |
| 22 | Diastereoisomer 1 | 2.7 ± 0.2 | ≥36 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (μM) | CC (μM) |
|---|---|---|---|
| 23 | Diastereoisomer 2 | 3.8 ± 0.3 | ≥36 |
| 24 | Diastereoisomer 1 | 10.6 ± 0.1 | 28.8 ± 1 |
| 25 | Diastereoisomer 2 | 6.3 ± 0.3 | 15.3 ± 0.2 |
| 26 | Diastereoisomer 1 | 7.5 ± 0.2 | 16.1 ± 0.2 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (µM) | CC (µM) |
|---|---|---|---|
| 27 | Diastereoisomer 2 | 8 ± 0.1 | 15.1 ± 0.2 |
| 28 | Diastereoisomer 1 | 8.9 ± 0.2 | 17.3 ± 0.1 |
| 29 | Diastereoisomer 2 | 5.9 ± 0.2 | 15.4 ± 0.3 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (μM) | CC (μM) |
|---|---|---|---|
| 30 | (structure) Diastereoisomer 1 | 11.2 ± 0.7 | 17 ± 0.7 |
| 31 | (structure) Diastereoisomer 1 | 5.1 ± 0.7 | 8.2 ± 0.3 |
| 32 | (structure) Stereoisomeric mixtures | 7.6 ± 0.8 | 13.7 ± 1 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (μM) | CC (μM) |
|---|---|---|---|
| 33 | Diastereoisomer 1 | 14 ± 0.1 | 28 ± 0.5 |
| 34 | Diastereoisomer 2 | 16 ± 0.1 | 34 ± 0.1 |
| 35 | Diastereoisomer 1 | 9 ± 0.2 | 25 ± 0.5 |
| 36 | Diastereoisomer 2 | 16.2 ± 0.2 | 31.5 ± 0.2 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (μM) | CC (μM) |
|---|---|---|---|
| 37 | Diastereoisomer 1 | 9.6 ± 0.1 | 30 ± 0.3 |
| 38 | Diastereoisomer 2 | 17 ± 0.2 | 34 ± 0.2 |
| 39 | Stereoisomer 1 | 2.1 ± 0.2 | ≥34 |
| 40 | Stereoisomer 2 | 6.5 ± 1.6 | ~40 |

TABLE 1-continued

Antiviral activity of small molecules in single cycle assy, TZM-bl cells infected with HIV-1 pseudovirus pseudotyped with HXB2 Env.

| Compound Number | Structure | TZM-bl | |
|---|---|---|---|
| | | IC$_{50}$ (μM) | CC (μM) |
| 41 | Stereoisomer 1 | 0.59 ± 0.06 | ≥33 |
| 42 | Stereoisomer 2 | 0.68 ± 0.03 | ≥33 |
| 43 | Stereoisomer 1 | 1.7 ± 0.4 | ≥34 |
| 44 | Stereoisomer 2 | 1.1 ± 0.1 | ≥34 |
| 45 | Stereoisomer 1 | >37 | >37 |

TABLE 1-continued
Antiviral activity of small molecules in single cycle assy, TZM-bl cells infected with HIV-1 pseudovirus pseudotyped with HXB2 Env.
| Compound Number | Structure | TZM-bl IC$_{50}$ (μM) | CC (μM) |
|---|---|---|---|
| 46 | 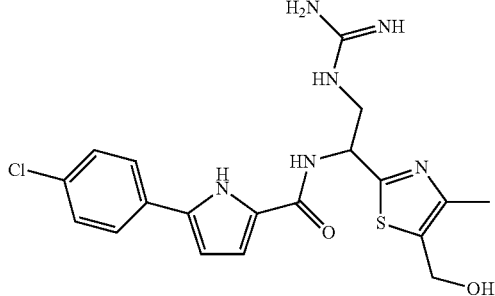<br>Stereoisomer 2 | ≥20 | >37 |
| 47 | 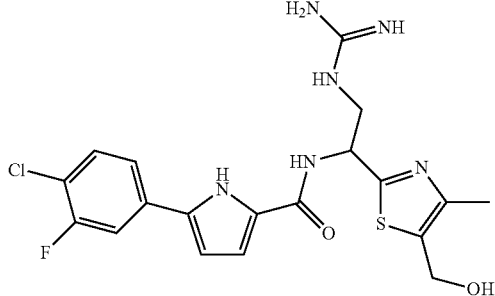<br>Stereoisomer 1 | ≥20 | >36 |
| 48 | 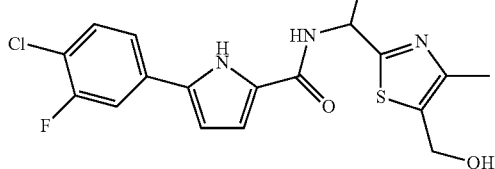<br>Stereoisomer 2 | >27 | >36 |
| 49 | 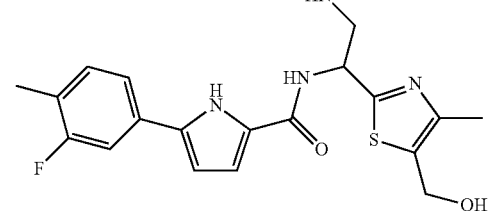<br>Stereoisomer 1 | ≥28 | >37 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (μM) | CC (μM) |
|---|---|---|---|
| 50 | Stereoisomer 2 | >20 | >37 |
| 51 | Stereoisomer 1 | 1.4 ± 0.5 | ~28 |
| 52 | Stereoisomer 2 | 0.89 ± 0.1 | 50.5 ± 1.3 |
| 53 | 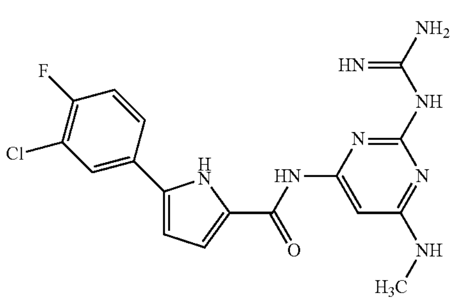 [SMILES: CNc1cc(NC(=O)c2ccc(-c3ccc(F)c(Cl)c3)[nH]2)nc(NC(=N)N)n1] | >36 | ≥36 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (μM) | CC (μM) |
|---|---|---|---|
| 54 | Stereoisomer 1 | 1.6 ± 0.6 | ~20 |
| 55 | Stereoisomer 2 | 2.1 ± 0.9 | ~40 |
| 56 | Stereoisomer 1 | ~0.6 | ~20 |
| 57 | Stereoisomer 2 | 1.6 ± 0.6 | ~21 |

TABLE 1-continued
Antiviral activity of small molecules in single cycle assy, TZM-bl cells infected with HIV-1 pseudovirus pseudotyped with HXB2 Env.
| Compound Number | Structure | TZM-bl $IC_{50}$ (μM) | CC (μM) |
|---|---|---|---|
| 58 | 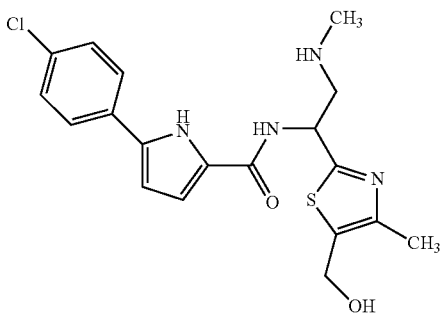 Stereoisomer 1 | 3.4 ± 0.6 | ~22 |
| 59 | 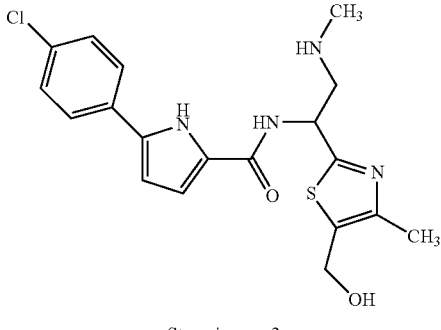 Stereoisomer 2 | 3.3 ± 0.5 | ~37 |
| 60 | 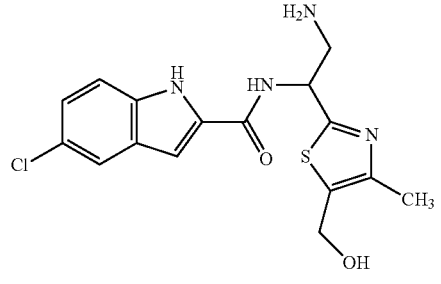 Stereoisomer 1 | >40 | ~47 |
| 61 | 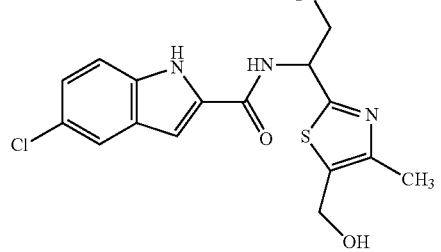 Stereoisomer 2 | ~50 | >55 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (µM) | CC (µM) |
|---|---|---|---|
| 62 | Stereoisomer 1 | >60 | >60 |
| 63 | Stereoisomer 2 | >60 | >60 |
| 64 | Stereoisomer 1 | ~40 | >44 |
| 65 | Stereoisomer 2 | ~40 | >44 |

TABLE 1-continued
Antiviral activity of small molecules in single cycle assy, TZM-bl cells infected with HIV-1 pseudovirus pseudotyped with HXB2 Env.
| Compound Number | Structure | TZM-bl IC$_{50}$ (μM) | CC (μM) |
|---|---|---|---|
| 66 | 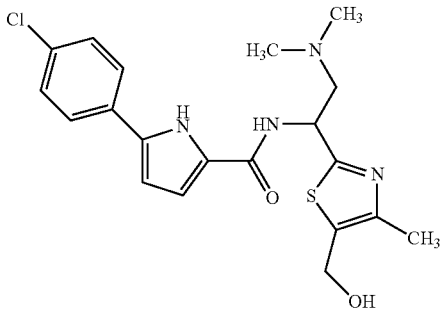 Stereoisomer 1 | 16.5 ± 3.4 | ~30 |
| 67 | 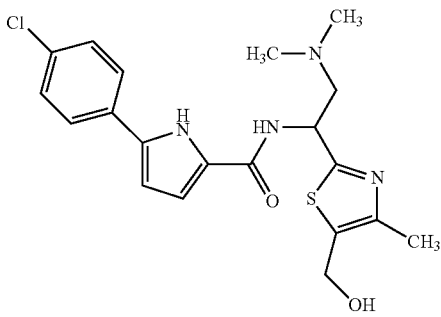 Stereoisomer 2 | 22 ± 3.8 | >40 |
| 68 | 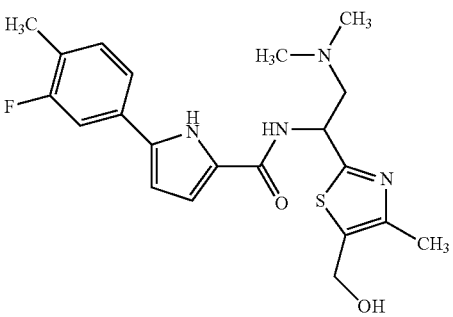 Stereoisomer 1 | 6.3 ± 1.8 | >40 |
| 69 | 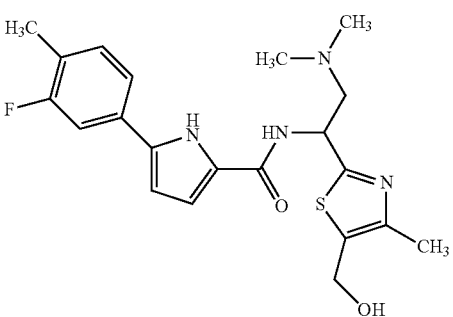 Stereoisomer 2 | ~40 | ~40 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (μM) | CC (μM) |
|---|---|---|---|
| 70 | Stereoisomer 1 | >40 | >40 |
| 71 | Stereoisomer 1 | 3.6 ± 1 | ~29 |
| 72 | Stereoisomer 2 | 7.2 ± 3 | ~29 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (μM) | CC (μM) |
|---|---|---|---|
| 73 | (Stereoisomer 1) | 2.2 ± 0.8 | 27.2 ± 0.8 |
| 74 | (Stereoisomer 2) | 1.1 ± 0.3 | 26.4 ± 0.7 |
| 75 | 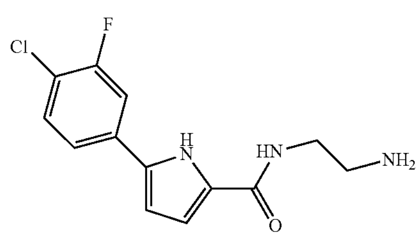 [SMILES: NCCNC(=O)c1ccc(-c2ccc(Cl)c(F)c2)[nH]1] | 3.3 ± 0.6 | 19.4 ± 0.9 |
| 76 | (Stereoisomer 1) | 11 ± 2.5 | 36.4 ± 1 |

TABLE 1-continued
Antiviral activity of small molecules in single cycle assy, TZM-bl cells infected with HIV-1 pseudovirus pseudotyped with HXB2 Env.
| Compound Number | Structure | TZM-bl $IC_{50}$ (μM) | CC (μM) |
|---|---|---|---|
| 77 | 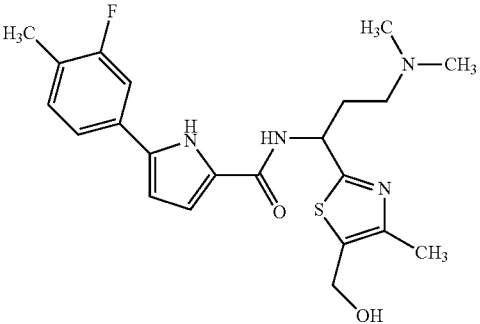 Stereoisomer 2 | 6.6 ± 0.2 | 37.1 ± 5.7 |
| 78 | 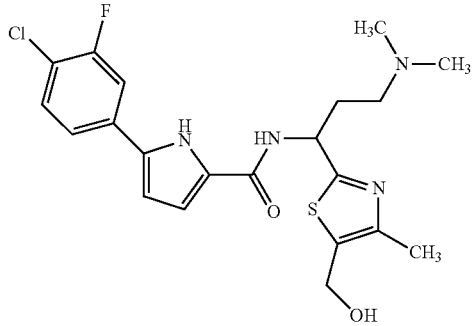 Stereoisomer 1 | 4.6 ± 0.2 | 22 ± 1 |
| 79 | 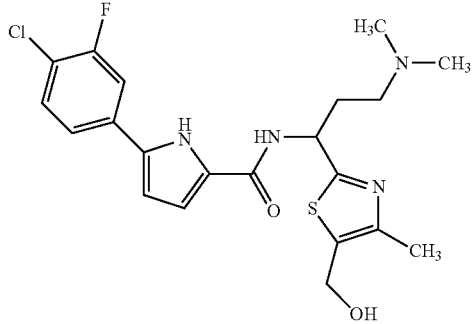 Stereoisomer 2 | 1.5 ± 0.3 | 21.3 ± 0.6 |
| 80 | 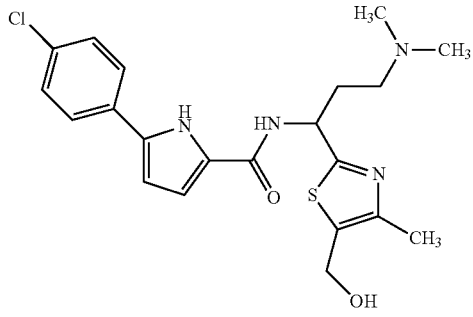 Stereoisomer 1 | 14.2 ± 0.7 | 21.7 ± 1 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (μM) | CC (μM) |
|---|---|---|---|
| 81 | Stereoisomer 2 | 10.4 ± 2 | 40.2 ± 3 |
| 82 | Stereoisomer 1 | 10.4 ± 0.2 | 36.4 ± 2.6 |
| 83 | Stereoisomer 2 | 1.6 ± 0.4 | 38.9 ± 2.1 |
| 84 | Stereoisomer 1 | 9.1 ± 1.1 | 22.3 ± 0.6 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (μM) | CC (μM) |
|---|---|---|---|
| 85 | Stereoisomer 2 | 1.5 ± 0.4 | 22 ± 0.6 |
| 86 | Stereoisomer 1 | 18.6 ± 1.5 | 23 ± 1.2 |
| 87 | Stereoisomer 2 | 1.7 ± 0.2 | 23 ± 0.6 |
| 88 | Stereoisomer 1 | 18.2 ± 2.6 | 47 ± 0.6 |

TABLE 1-continued
Antiviral activity of small molecules in single cycle assy, TZM-bl cells infected with HIV-1 pseudovirus pseudotyped with HXB2 Env.
| Compound Number | Structure | TZM-bl IC$_{50}$ (μM) | CC (μM) |
|---|---|---|---|
| 89 | 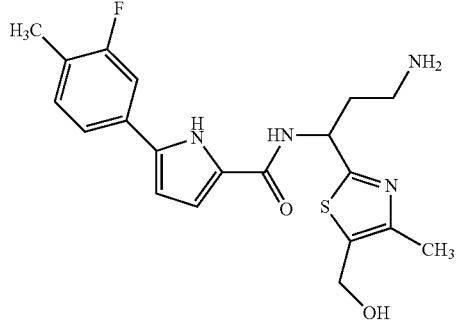 Stereoisomer 2 | 4.2 ± 1.7 | 43.8 ± 1.6 |
| 90 | 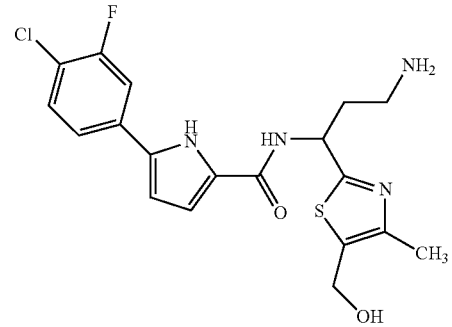 Stereoisomer 1 | 4.1 ± 1.5 | 22.9 ± 0.6 |
| 91 | 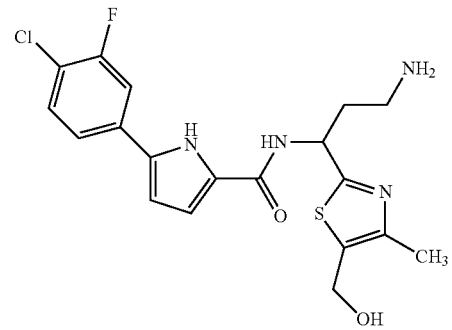 Stereoisomer 2 | 6.6 ± 2 | 35 ± 3 |
| 92 | 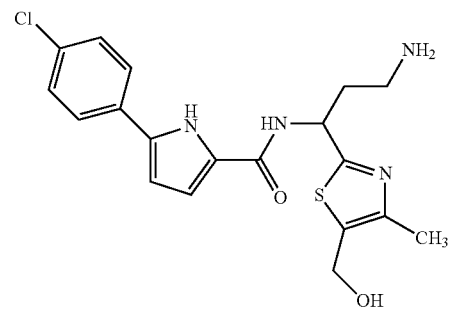 Stereoisomer 1 | 18.7 ± 0.7 | 41 ± 1.1 |

TABLE 1-continued
Antiviral activity of small molecules in single cycle assy, TZM-bl cells infected with HIV-1 pseudovirus pseudotyped with HXB2 Env.
| Compound Number | Structure | TZM-bl IC$_{50}$ (µM) | CC (µM) |
|---|---|---|---|
| 93 | 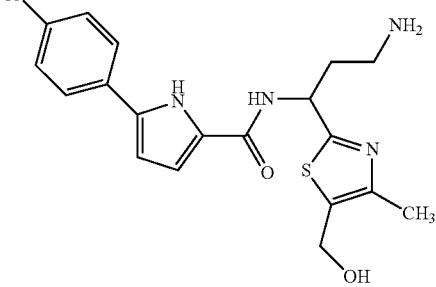 Stereoisomer 2 | 4 ± 0.3 | 41 ± 1 |
| 94 | 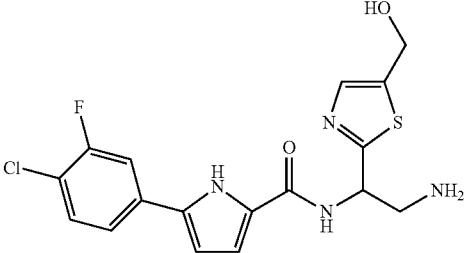 Stereoisomer 1 | 1.1 ± 0.8 | 37.4 ± 0.3 |
| 95 | 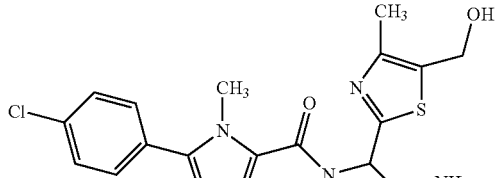 Stereoisomer 1 | 26 ± 1.4 | 35.8 ± 0.3 |
| 96 | 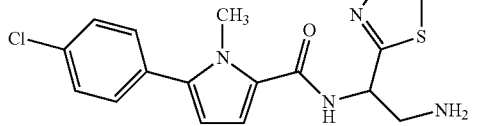 Stereoisomer 2 | 25.8 ± 1.1 | 36.7 ± 0.4 |
| 97 | 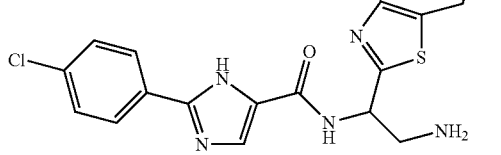 Stereoisomer 1 | >51 | >51 |

TABLE 1-continued

Antiviral activity of small molecules in single cycle assy, TZM-bl cells infected with HIV-1 pseudovirus pseudotyped with HXB2 Env.

| Compound Number | Structure | TZM-bl IC$_{50}$ (μM) | CC (μM) |
|---|---|---|---|
| 98 | Stereoisomer 2 | >51 | >51 |
| 99 | Stereoisomer 1 | 34.9 ± 3 | >51 |
| 100 | Stereoisomer 2 | ~51 | >51 |
| 101 | Stereoisomer 1 | 3.6 ± 0.4 | 22.2 ± 0.3 |
| 102 | Stereoisomer 2 | 2.6 ± 0.1 | 5.2 ± 0.3 |

Example 3

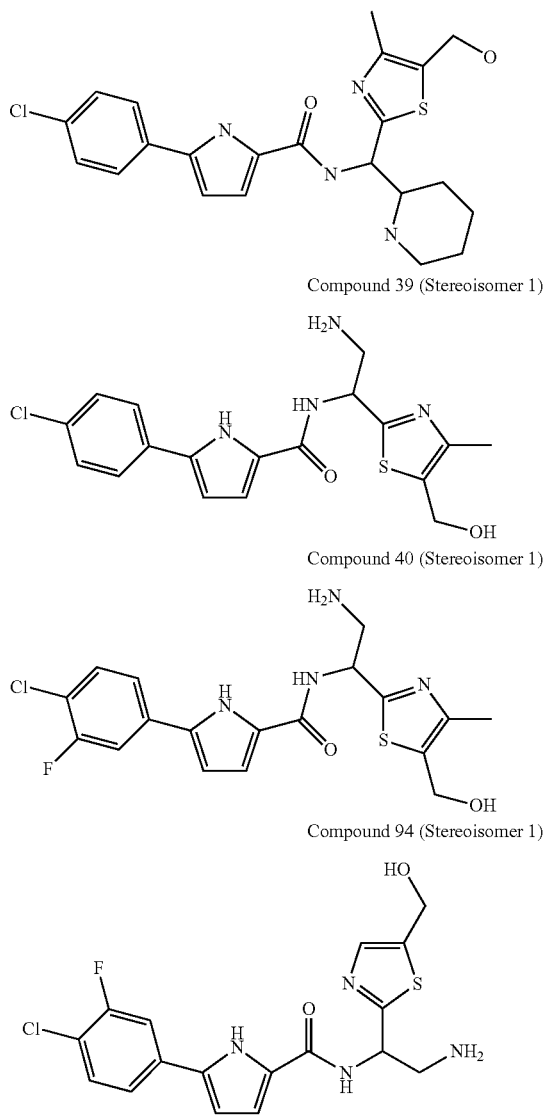

Compound 15 (Stereoisomeric mixtures)

Compound 39 (Stereoisomer 1)

Compound 40 (Stereoisomer 1)

Compound 94 (Stereoisomer 1)

Example 4

Cell-to-Cell Fusion

To assess the ability of NBD-compounds to block cell-to-cell fusion mediated by HIV-1 we performed cell fusion assay as previously described 3[1-3] with some modifications. We used MAGI-CCR5 cells, a HeLa cell clone expressing human CD4, both co-receptors CXCR4 and CCR5 and HIV-LTR-β-gal[2,4] as target cells and HL 2/3 cells, a HeLa-derived cell line which express HIV-1$_{HXB2}$ Env on the surface and Tat, Gag, Rev and Nef proteins in the cytoplasm and does not produce detectable amounts of mature virions[5] as effector cells. Following fusion of the two cell lines Tat induce the expression of β-gal enzyme. Briefly, following pre-incubation of $1.5 \times 10^4$/well MAGI-CCR5 cells for 1 hr with escalating concentrations of NBD-compounds, $7.5 \times 10^3$/well HL 2/3 cells were added to the culture and incubated for 24 h at 37° C. β-gal expression was quantified with the Beta-Glo® Assay System (Promega) following the manufacturer's instructions. The percent inhibition and the $IC_{50}$ values were calculated using the Graph Pad Prism software. (See Table 3)

In Vitro Biochemical HIV RT and Integrase Assay

Purified recombinant HIV (pNL4-3) heterodimeric (p66/p51) Reverse Transcriptase (RT) was purchased from a commercially available source. The assay was performed in 96-well filter plate, where RT activity was determined by the incorporation of radiolabeled deoxyribonucleotides into the newly synthesized DNA strand. The standard RT reaction mixture contains in vitro transcribed viral RNA derived from the HIV-1$_{NL4-3}$ 5'-LTR region (position 454 to 652) and primer that is complementary to the primer binding site (PBS, nucleotide residues nucleotides 636 to 652), radiolabeled deoxyribonucleotide, dNTPs and reverse transcriptase. Briefly, the reaction was carried out in a volume of 50 μl containing 50 mM Tris HCl, pH 7.8, 50 mM KCl, 5 mM $MgCl_2$, 1 mM DTT, 50 μM each of dATP, dCTP, dGTP, 50 nM dTTP, 1 μCi of [$^3$H] dTTP (70-90 Ci/mM) and 5 nM template/primer. The reaction was initiated by the addition of 10 nM RT.

Compounds were diluted in 100% DMSO to 40 mM. Each compound was diluted in the appropriate reaction buffer for the biochemical assay per protocol. Serially diluted test compounds were added to the reaction followed by the addition of RT. The reaction mixture was incubated at 37° C. for 1 h, and then quenched by the addition of ice-cold trichloroacetic acid (TCA) to the final concentration of 10%. The plate was incubated at 4° C. for 1 h to precipitate the synthesized DNA, then rinsed 3-times with 10% TCA and 1 time with 70% ethanol. After addition of 25 μl scintillation fluid to completely dried wells, radioactivity was counted by MicroBeta scintillation counter (PerkinElmer). The reduction of radioactivity represents the potency of compound inhibition. (See Table 3)

HIV-1 Integrase was performed as per the protocol in the HIV-1 Integrase Assay Kit from ExpressBio (Thurnmont, Md.). (See Table 3)

Multi-Cycle Infection Assay in MT-2 Cells.

The inhibitory activity of test compounds on infection by laboratory-adapted HIV-1 strains was determined as previously described[6]. Briefly, $1 \times 10^4$ MT-2 cells were infected with HIV-1$_{IIIB}$ and other lab-adapted HIV-1 at 100 $TCID_{50}$ (0.01 MOI) in the presence or absence of test compounds at graded concentrations overnight. The culture supernatants were then removed and fresh media were added. On the fourth day post-infection, 100 μl of culture supernatants were collected from each well, mixed with equal volume of 5% Triton X-100 and tested for p24 antigen by "sandwich" ELISA. (See Table 4)

Multi-Cycle Infection Assay in PBMC.

The inhibitory activity of test compounds on infection by primary HIV-1 isolates was determined as previously described[6]. PBMCs were isolated from the blood of healthy donors at the New York Blood Center by standard density gradient centrifugation using Histopaque-1077 (Sigma-Aldrich). The cells were cultured at 37° C. for 2 hr. Non-adherent cells were collected and cultured at $5 \times 10^6$ cells/ml RPMI-1640 medium containing 10% FBS, 5 μg/ml PHA, and 100 U/ml IL-2 (Sigma-Aldrich), followed by incubation at 37° C. for 3 days. The PHA-stimulated cells ($5 \times 10^4$ cells/well) were infected with lab-adapted and primary HIV-1 isolates at 500 $TCID_{50}$ (0.01 MOI) in the absence or presence of inhibitors at graded concentrations. Culture media were replaced every 3 days with fresh media. The supernatants were collected 7 days post-infection and tested for p24 antigen by ELISA. The percent inhibition of p24 production and $IC_{50}$ values were calculated by the GraphPad Prism software. (See Table 4)

Determination of Cytotoxicity

MT-2 Cells.

Cytotoxicity of test compounds in MT-2 cells was measured a by colorimetric method using XTT [(sodium 3'-(1-(phenylamino)-carbonyl)-3,4-tetrazolium-bis(4-methoxy-6-nitro) benzenesulfonic acid hydrate)] (PolySciences) as previously described[7]. Briefly, 100 μl of a test compound at graded concentrations was added to an equal volume of cells ($1 \times 10^5$ cells/ml) in 96 well plates followed by incubation at 37° C. for 4 days, which ran parallel to the neutralization assay in MT-2. Following the addition of XTT the soluble intracellular formazan was quantitated colorimetrically at 450 nm 4 h later. The percent of cytotoxicity and the $CC_{50}$ (the concentration for 50% cytotoxicity) values were calculated by the GraphPad Prism software. (See Table 4)

TZM-Bl Cells.

The cytotoxicity of test compounds in TZM-bl cells was also measured by the XTT method described previously[7]. Briefly, 100 μl of a compound at graded concentrations was added to equal volume of cells ($10^5$/ml) in wells of 96 well plates followed by incubation at 37° C. for 3 days and addition of XTT. The soluble intracellular formazan was quantitated colorimetrically at 450 nm 4 h later. The percent of cytotoxicity and the $CC_{50}$ values were calculated as above. (See Table 4)

PBMC.

For the PBMC toxicity assay we used $5 \times 10^5$ cells/ml and the cytotoxicity of the compounds was measured after 7 days of incubation as previously reported. Following the addition of XTT the soluble intracellular formazan was quantitated colorimetrically at 450 nm 4 h later. The percent of cytotoxicity and the $CC_{50}$ values were calculated as above. (See Table 4)

TABLE 2

Inhibitory activity of Compound 1 and Compound 2 against a panel of HIV-1 ENV-pseudoviruses

| Subtype | NIH # | ENVs | $IC_{50}$ (μM) ± S.D.[#] | | | | |
|---|---|---|---|---|---|---|---|
| | | | Compound 15 | Compound 17 | Compound 19 | Compound 39 | Compound 40 |
| A | 11887 | Q259env.w6 | 2.8 ± 0.1 | 1.6 ± 0.1 | 1.3 ± 0.4 | 1.3 ± 0.02 | 0.74 ± 0.06 |
| | 11888 | QB726.70M.ENV.C4 | 2.6 ± 0.1 | 1.3 ± 0.3 | 1.5 ± 0.6 | 0.8 ± 0.3 | 0.62 ± 0.04 |
| | 11889 | QB726.70M.ENV.B3 | 1.5 ± 0.9 | 1.3 ± 0.4 | 2.4 ± 0.9 | 2.4 ± 0.6 | 1.1 ± 0.03 |
| | 11890 | QF495.23M.ENV.A1 | 1.8 ± 0.5 | 1.3 ± 0.4 | 0.86 ± 0.4 | 1.2 ± 0.3 | 0.64 ± 0.04 |
| | 11891 | QF495.23M.ENV.A3 | 3.2 ± 0.4 | 0.88 ± 1.4 | 1.3 ± 0.3 | 2.5 ± 0.2 | 1.2 ± 0.06 |
| | 11892 | QF495.23M.ENV.B2 | 3.7 ± 1 | 0.6 ± 0.4 | 1.1 ± 0.2 | 1.1 ± 0.2 | 0.52 ± 0.07 |
| | | BG505-T332N | 2.4 ± 1 | 1 ± 0.1 | 1.3 ± 0.6 | 0.78 ± 0.2 | 0.33 ± 0.04 |
| | | KNH1144 | 2.1 ± 0.1 | 2.1 ± 0.4 | 2.3 ± 0.2 | 0.67 ± 0.02 | 0.43 ± 0.2 |
| A/D | 11901 | QA790.204I.ENV.A4 | 3.7 ± 0.2 | 1.4 ± 0.05 | 1 ± 0.3 | 2.1 ± 0.3 | 0.62 ± 0.02 |
| | 11903 | QA790.204I.ENV.C8 | 2 ± 0.1 | 1.6 ± 0.2 | 1.6 ± 0.2 | 2.5 ± 0.1 | 1 ± 0.09 |
| | 11904 | QA790.204I.ENV.E2 | 3.4 ± 0.1 | 1.2 ± 0.3 | 2 ± 0.05 | 2.3 ± 0.6 | 0.92 ± 0.02 |
| A2/D | 11906 | QG393.60M.ENV.B7 | 1.7 ± 0.2 | 0.8 ± 0.3 | 1.4 ± 0.5 | 1.1 ± 0.1 | 0.39 ± 0.02 |
| A/E(potential) | 11603 | CRF01_AE clone 269 | 3 ± 0.1 | 1.5 ± 0.3 | 1.7 ± 0.9 | 2 ± 0.2 | 0.7 ± 0.02 |
| A/G | 11601 | CRF02_AG clone 263 | 2.2 ± 0.3 | 1.4 ± 0.3 | 2.2 ± 0.7 | 1.5 ± 0.2 | 0.59 ± 0.09 |
| | 11602 | CRF02_AG clone 266 | 1.6 ± 0.5 | 1 ± 0.2 | 1.3 ± 0.5 | 1.6 ± 0.2 | 0.68 ± 0.02 |
| | 11605 | CRF02_AG clone 278 | 2.2 ± 0.4 | 1.3 ± 0.5 | 1.8 ± 0.2 | 1.1 ± 0.2 | 0.68 ± 0.02 |
| B | | B41 | 1.1 ± 0.1 | 0.68 ± 0.1 | 1.1 ± 0.4 | 0.32 ± 0.02 | 0.28 ± 0.03 |
| | 11578 | pWEAUd15.410.5017 | 3 ± 0.1 | 3 ± 0.1 | 1.7 ± 0.03 | 0.67 ± 0.1 | 0.28 ± 0.04 |
| | 11018 | QH0692, clone 42 | 0.7 ± 0.2 | 0.52 ± 0.1 | 0.9 ± 0.3 | 1.6 ± 0.2 | 0.49 ± 0.05 |
| | 11022 | PVO, clone 4 | 1.7 ± 0.1 | 1.9 ± 0.1 | 1.1 ± 0.2 | 1.3 ± 0.3 | 0.74 ± 0.07 |
| | 11023 | TRO, clone 11 | 1.3 ± 0.2 | 1.2 ± 0.05 | 1 ± 0.1 | 1.4 ± 0.04 | 0.51 ± 0.09 |
| | 11024 | AC10.0, clone 29 | 1 ± 0.2 | 0.32 ± 0.01 | 0.74 ± 0.25 | 0.54 ± 0.1 | 0.29 ± 0.03 |
| | 11033 | pWITO4160 clone 33 | 2 ± 0.05 | 1.7 ± 0.1 | 1 ± 0.2 | 1.1 ± 0.2 | 0.5 ± 0.06 |
| | 11035 | pREJO4541 clone 67 | 1.8 ± 0.2 | 1.6 ± 0.3 | 1.2 ± 0.1 | 1 ± 0.2 | 0.43 ± 0.03 |
| | 11036 | pRHPA4259 clone 7 | 2.1 ± 0.1 | 2 ± 0.4 | 1.2 ± 0.06 | 1.1 ± 0.1 | 1 ± 0.1 |
| | 11037 | pTHRO4156 clone 18 | 3.1 ± 1.6 | 1 ± 0.2 | 2 ± 0.2 | 0.82 ± 0.08 | 0.69 ± 0.08 |
| | 11038 | pCAAN5342 clone A2 | 1.7 ± 0.1 | 0.6 ± 0.07 | 0.64 ± 0.01 | 1.4 ± 0.4 | 0.47 ± 0.1 |
| | 11058 | SC422661.8 | 0.6 ± 0.1 | 0.33 ± 0.01 | 0.27 ± 0.02 | 0.77 ± 0.1 | 0.57 ± 0.05 |
| C | 11306 | Du156, clone 12 | 2.9 ± 0.6 | 2.2 ± 0.5 | 1.2 ± 0.2 | 1.3 ± 0.08 | 0.43 ± 0.08 |
| | 11307 | Du172, clone 17 | 1.5 ± 0.3 | 1.9 ± 0.5 | 1.5 ± 0.3 | 0.78 ± 0.1 | 0.59 ± 0.06 |
| | 11308 | Du422, clone 1 | 3 ± 0.1 | 3.3 ± 0.4 | 2 ± 0.6 | 0.81 ± 0.2 | 0.62 ± 0.06 |
| | 11309 | ZM197M.PB7 | 2 ± 0.2 | 2.2 ± 0.5 | 0.96 ± 0.2 | 2 ± 0.4 | 1.2 ± 0.09 |
| | 11310 | ZM214M.PL15 | 2.6 ± 0.1 | 2.7 ± 0.2 | 1.7 ± 0.6 | 1.1 ± 0.1 | 0.42 ± 0.03 |
| | 11311 | ZM233M.PB6 | 1.4 ± 0.2 | 1.3 ± 0.1 | 1.2 ± 0.1 | 0.91 ± 0.04 | 1 ± 0.06 |
| | 11312 | ZM249M.PL1 | 3.1 ± 0.3 | 3.1 ± 0.5 | 1.8 ± 0.6 | 2.4 ± 0.4 | 1 ± 0.1 |
| | 11313 | ZM53M.PB12 | 1.3 ± 0.2 | 1.5 ± 0.2 | 1.3 ± 0.3 | 1.6 ± 0.2 | 0.6 ± 0.04 |
| | 11314 | ZM109F.PB4 | 2.2 ± 0.4 | 3.2 ± 0.5 | 1.9 ± 0.3 | 2.5 ± 0.1 | 0.95 ± 0.2 |
| D | 11912 | QA013.70I.ENV.M12 | 2.4 ± 0.2 | 2.2 ± 0.3 | 1.7 ± 0.2 | 0.54 ± 0.07 | 0.3 ± 0.01 |
| | 11916 | QD435.100M.ENV.B5 | 2 ± 0.6 | 1.7 ± 0.5 | 1.7 ± 0.6 | 1.9 ± 0.2 | 1.2 ± 0.1 |
| | 11918 | QD435.100M.ENV.E1 | 4 ± 0.8 | 3.7 ± 0.1 | 2.7 ± 0.5 | 0.52 ± 0.3 | 0.46 ± 0.09 |

TABLE 3

Antiviral activity of NBD compounds in a HIV-1 cell-cell fusion assay, and in assays using HIV-1 reverse transcriptase (RT) and integrase enzymes.

| Inhibitors | $IC_{50}$ (μM) |
|---|---|
| Cell-Cell fusion Assay | |
| Compound 15 | 9.8 |
| Compound 17 | 10.8 |

TABLE 3-continued

Antiviral activity of NBD compounds in a
HIV-1 cell-cell fusion assay, and in assays using
HIV-1 reverse transcriptase (RT) and integrase enzymes.

| Inhibitors | $IC_{50}$ (µM) |
|---|---|
| Compound 19 | 7.6 |
| NBD-556 | 6.5 |
| BMS-378806 (control) | 0.014 |
| HIV-1 Reverse Transcriptase (RT) assay | |
| Compound 17 | 43.4 |
| Compound 39 | 2.56 |
| Compound 94 | 2.72 |
| NBD-556 | >200 |
| Nevirapine (control) | 0.20 |
| AZT-TP (control) | 0.008 |
| HIV-1 Integrase Assay | |
| Compound 17 | >100 |
| Compound 39 | >100 |
| Compound 94 | >100 |
| NBD-556 | >200 |
| Raltegravir (control) | 0.21 |

TABLE 4

Antiviral activity of the NBD compounds in laboratory-adapted
and primary HIV-1 isolates and toxicity values

| HIV-1 virus | Subtype | Cell Type | Co-receptor | $IC_{50}$ (µm) NBD-556 | NBD-09027 | Compound 15 |
|---|---|---|---|---|---|---|
| Laboratory Strains | | | | | | |
| IIIB | B | MT-2 | X4 | 6.5 ± 0.1 | 4.7 ± 0.6 | 3.46 ± 0.2 |
| MN | B | MT-2 | X4 | 15.9 ± 1.6 | 4 ± 0.9 | 2.1 ± 0.1 |
| SF2 | B | MT-2 | R5X4 | ≥118 | 5.7 ± 0.9 | 2.6 ± 0.3 |
| RF | B | MT-2 | R5X4 | 18.7 ± 1.3 | 9.6 ± 0.8 | 7.3 ± 0.6 |
| BaL | B | PBMC | R5 | ≥118 | 35.8 ± 1.2 | 3.7 ± 0.4 |
| 89.6 | B | PBMC | R5X4 | 4.8 ± 1 | 6.7 ± 0.3 | 1.2 ± 0.1 |
| SF162 | B | PBMC | R5 | 48.9 ± 7.3 | 12.7 ± 0.7 | 2.6 ± 0.5 |
| RT-Resistant Isolate | | | | | | |
| AZT-R | B | MT-2 | X4 | 58 ± 14.3 | 4.4 ± 1.1 | 3 ± 0.1 |
| Protease Resistant Isolate | | | | | | |
| HIV-1$_{RF/L-323-12-3}$ | B | MT-2 | X4 | >59 | 14.7 ± 2.3 | 6.7 ± 0.3 |
| Fusion Resistant Isolate | | | | | | |
| pNL4-3 gp41$_{(36G) V38E, N42S}$ | B | MT-2 | X4 | 11 ± 0.9 | 5.8 ± 0.3 | 2.2 ± 0.1 |
| Primary isolates | | | | | | |
| 92US657 | B | PBMC | R5 | 48 ± 1.65 | 8.6 ± 0.9 | 3.3 ± 0.9 |
| 93IN101 | C | PBMC | R5 | — | >87 | 2.9 ± 0.1 |
| 93MW959 | C | PBMC | R5 | 57.2 ± 8.7 | >43.5 | 2.3 ± 0.5 |
| 93TH060 | E | PBMC | R5 | >45 | 7.2 ± 0.6 | 5.5 ± 1.2 |
| RU570 | G | PBMC | R5 | 19.5 ± 2.3 | 8.5 ± 0.8 | 2.5 ± 0.6 |
| BCF02 | (Group O) | PBMC | R5 | — | ~87 | 9.6 ± 1.1 |

| | NBD-556 | NBD-09027 | NBD-11021 |
|---|---|---|---|
| MT-2 $CC_{50}$ (µM) | >280 | >108 | ~28 |
| PBMC $CC_{50}$ (µM) | >280 | >160 | ~36 |

>indicating that 50% toxicity or activity respect to the untreated control at this dose was not reached The foregoing description details specific methods and compositions that can be employed to make and use the compounds described herein, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the scope of the claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A compound represented by Formula 1:

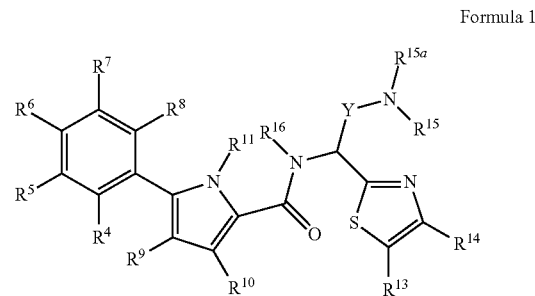

Formula 1 wherein $R^4$, $R^5$, $R^6$, $R^7$, $R^8$, $R^9$, $R^{10}$, $R^{12}$, $R^{13}$, and $R^{14}$ are H, a halide, or a substituent having a molecular weight of 15 Da to 150 Da and consisting of 2 to 5 chemical elements, wherein the chemical elements are independently C, H, O, N, S, P, F, Cl, Br, or I;

$R^{11}$ is H, optionally substituted $C_{1-6}$ alkyl, the optional substituent having a molecular weight of 15 Da to 150 Da and consisting of 2 to 5 chemical elements, wherein the chemical elements are independently C, H, O, N, S, P, F, Cl, Br, or I;

$R^{15}$, and $R^{15a}$ are H, optionally substituted $C_{1-6}$ alkyl, optionally substituted carbamimidoyl, optionally substituted $C_{1-6}$ aryl, or optionally substituted $C_{1-6}$ heteroaryl, the optional substituent having a molecular weight of 15 Da to 150 Da and consisting of 2 to 5 chemical elements, wherein the chemical elements are independently C, H, O, N, S, P, F, Cl, Br, or I;

$R^{16}$ is H or $C_{1-6}$ hydrocarbyl; and

Y is a bond or $C_{1-3}$ alkyl.

2. The compound of claim 1, wherein Y—N($R^{15}$, $R^{15a}$) is —CH$_2$NH$_2$.

3. The compound of claim 1, wherein Y—N($R^{15}$, $R^{15a}$) is —CH$_2$CH$_2$NH$_2$.

4. The compound of claim 1, wherein Y—N($R^{15}$, $R^{15a}$) is —CH$_2$NHCH$_3$.

5. The compound of claim 1, wherein [Y—N($R^{15}$, $R^{15a}$) is —CH$_2$N(CH$_3$)$_2$.

6. The compound of claim 1, wherein Y—N($R^{15}$, $R^{15a}$) is —CH$_2$CH$_2$N(CH$_3$)$_2$.

7. The compound of claim 1, wherein Y—N($R^{15}$, $R^{15a}$) is —CH$_2$CH$_2$NHCH$_3$.

8. A compound represented by a formula:

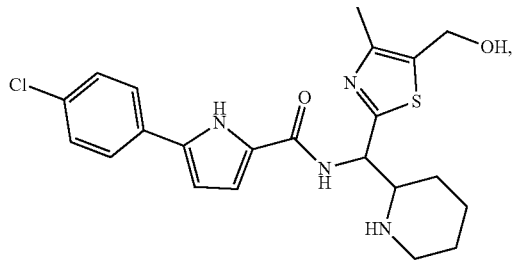

85
-continued
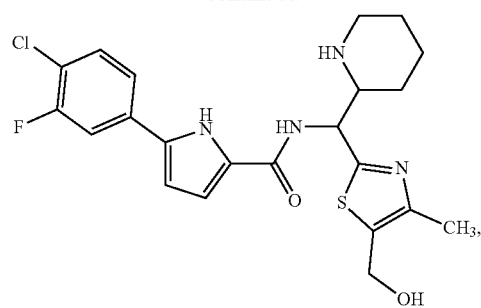
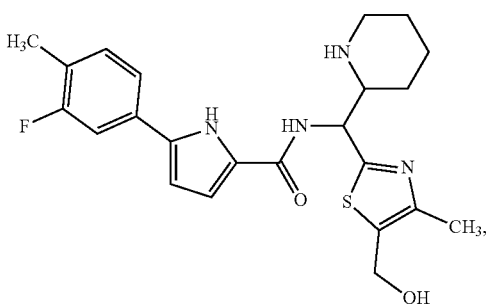
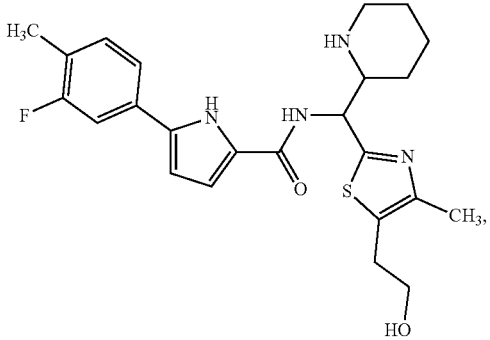
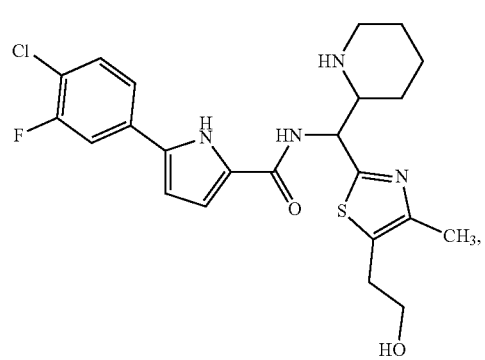
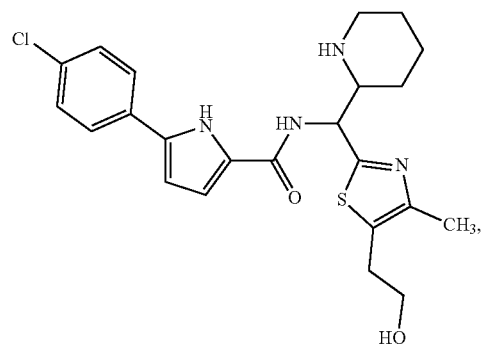
86
-continued
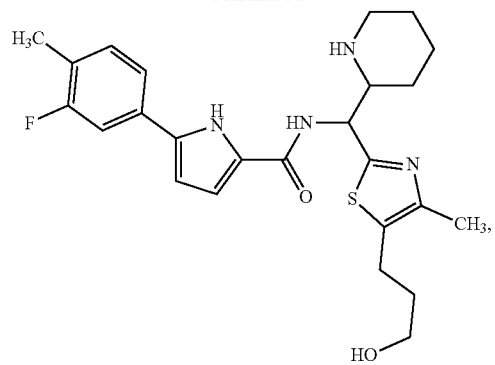
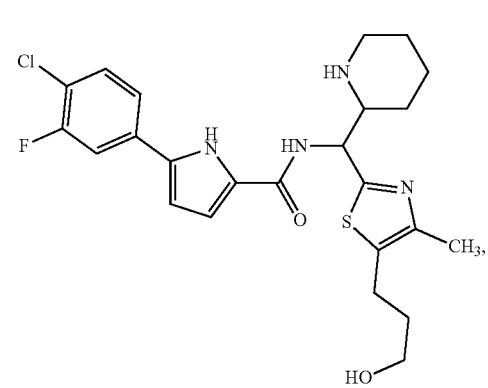
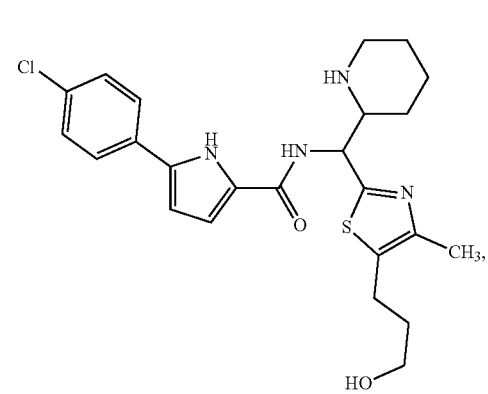
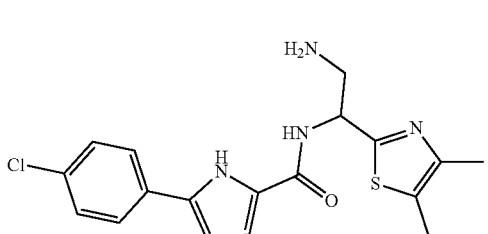
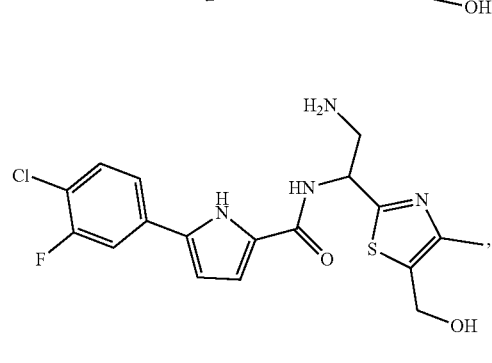

-continued

89
-continued
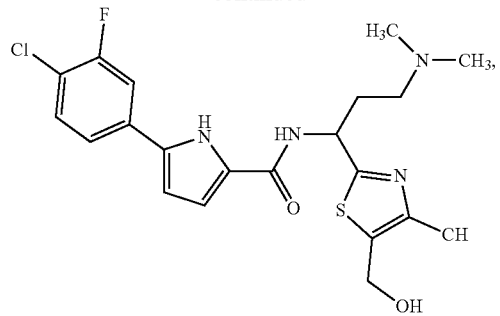
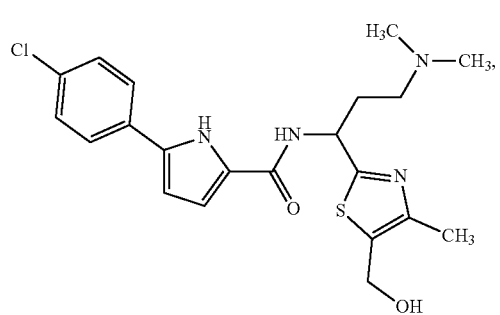
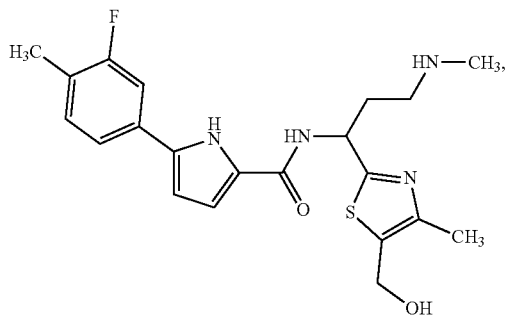
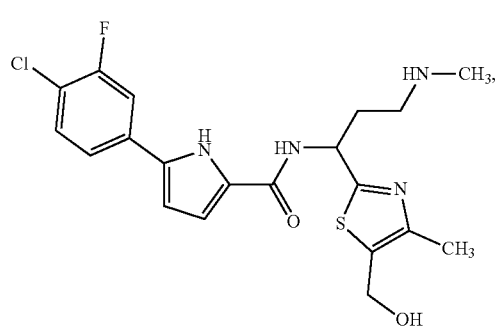
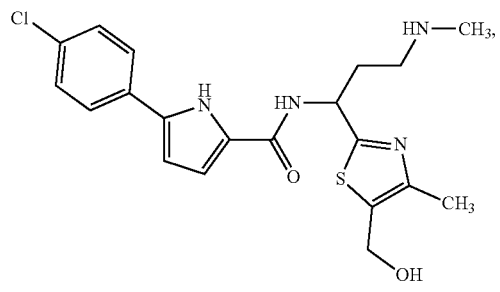
90
-continued
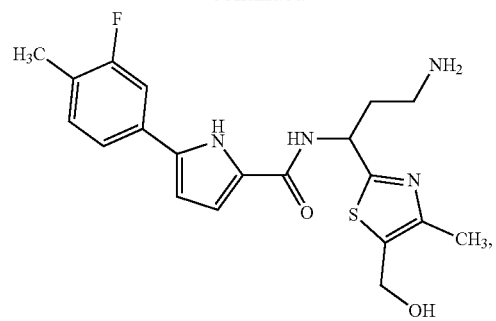
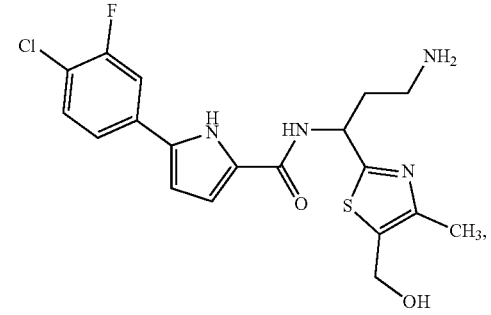
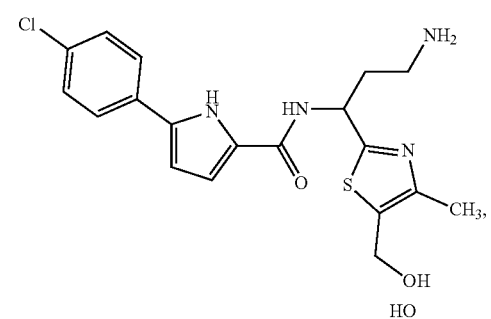
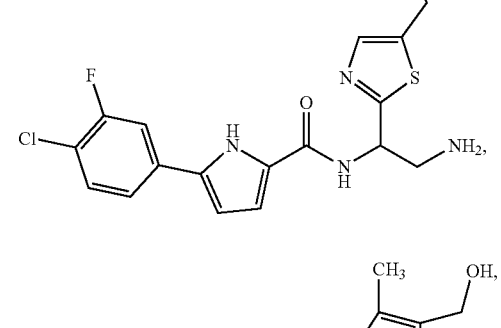
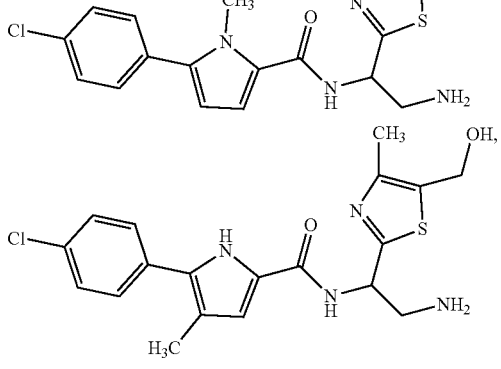

-continued

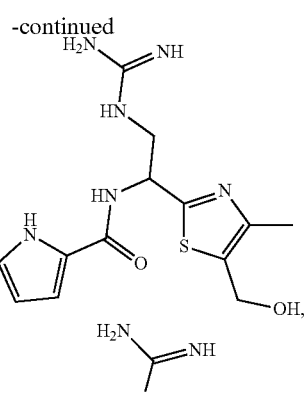

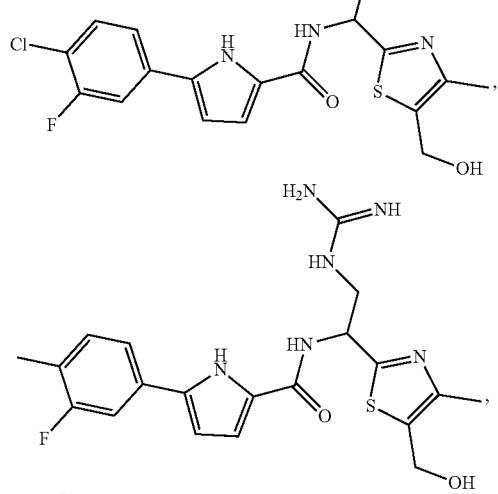

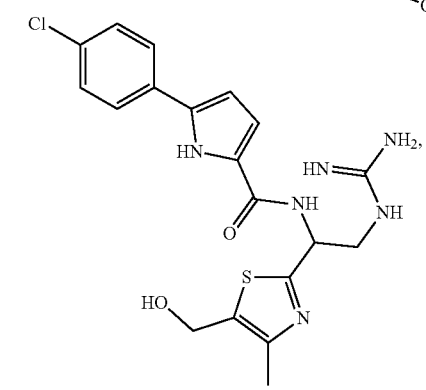

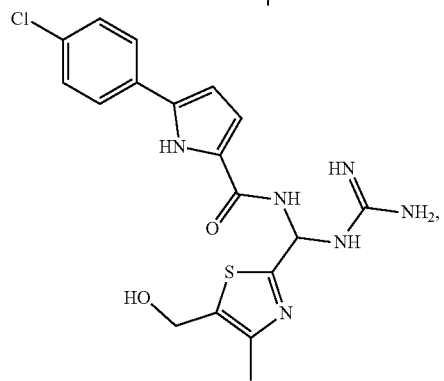

-continued

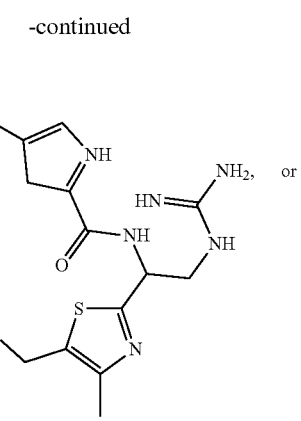

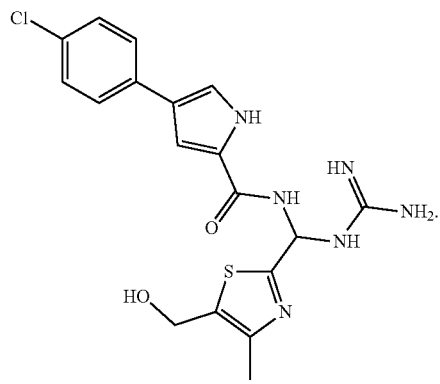

9. A method of treating HIV infection comprising administering a compound according to claim 1 to a human being infected with HIV virus.

10. The compound of claim 1, wherein Y—N($R^{15}$, $R^{15a}$) is:

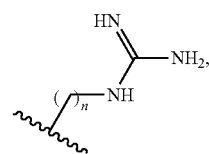

wherein n is 0, 1, or 3.

11. The compound of claim 1, wherein $R^{11}$ is H.

12. The compound of claim 1, wherein $R^6$ is a halide.

13. The compound of claim 1, wherein $R^6$ is $CH_3$.

14. The compound of claim 1, wherein $R^5$ or $R^7$ is a halide.

15. The compound of claim 14, wherein $R^5$ or $R^7$ is F.

16. The compound of claim 1, wherein $R^{13}$ is —$(CH_2)_n$OH, wherein n is 1, 2, or 3.

17. The compound of claim 1, wherein $R^{14}$ is $CH_3$ or H.

18. The compound of claim 1, wherein $R^{15}$ and $R^{15a}$ are, independently, H, $CH_3$, or carbamimidoyl.

* * * * *

UNITED STATES PATENT AND TRADEMARK OFFICE
CERTIFICATE OF CORRECTION

PATENT NO. : 10,137,107 B2
APPLICATION NO. : 15/512493
DATED : November 27, 2018
INVENTOR(S) : Asim Kumar Debnath et al.

Page 1 of 1

It is certified that error appears in the above-identified patent and that said Letters Patent is hereby corrected as shown below:

On the Title Page

Item (73) Assignees, 'National Institutes of Health, Bethesda, MD (US)' should read -The United States of America, as Represented by the Secretary, Department of Health and Human Services, Washington, DC (US)-.

Signed and Sealed this
Twenty-second Day of October, 2019

Andrei Iancu
*Director of the United States Patent and Trademark Office*